(12) United States Patent
Kodama et al.

(10) Patent No.: US 9,976,126 B2
(45) Date of Patent: May 22, 2018

(54) MODIFIED GLYCINE OXIDASE

(71) Applicant: AJINOMOTO CO., INC., Tokyo (JP)

(72) Inventors: Yuya Kodama, Kanagawa (JP);
Wataru Hoshino, Kanagawa (JP);
Kazutoshi Takahashi, Kanagawa (JP);
Moemi Ito, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 168 days.

(21) Appl. No.: 14/862,323

(22) Filed: Sep. 23, 2015

(65) Prior Publication Data

US 2016/0002610 A1 Jan. 7, 2016

Related U.S. Application Data

(63) Continuation of application No. PCT/JP2014/059353, filed on Mar. 28, 2014.

(30) Foreign Application Priority Data

Mar. 29, 2013 (JP) .................................. 2013-073906

(51) Int. Cl.
| | | |
|---|---|---|
| *C12N 9/00* | (2006.01) | |
| *C12Q 1/26* | (2006.01) | |
| *C12P 7/42* | (2006.01) | |
| *C12P 7/40* | (2006.01) | |
| *C12Q 1/00* | (2006.01) | |
| *G01N 27/327* | (2006.01) | |
| *C12N 9/06* | (2006.01) | |

(52) U.S. Cl.
CPC .............. *C12N 9/0022* (2013.01); *C12P 7/40* (2013.01); *C12P 7/42* (2013.01); *C12Q 1/005* (2013.01); *C12Q 1/26* (2013.01); *C12Y 104/03019* (2013.01); *G01N 27/3271* (2013.01); *G01N 2333/90638* (2013.01)

(58) Field of Classification Search
None
See application file for complete search history.

(56) References Cited

U.S. PATENT DOCUMENTS

| 7,833,397 B2 | 11/2010 | Kimura |
|---|---|---|
| 8,440,068 B2 | 5/2013 | Kimura |
| 2015/0010936 A1 | 1/2015 | Hoshino et al. |

FOREIGN PATENT DOCUMENTS

| EP | 0101945 A1 | 7/1984 |
|---|---|---|
| JP | 59-020853 A | 2/1984 |
| WO | WO2005/075970 A1 | 8/2005 |

OTHER PUBLICATIONS

Pedotti et al., "Glyphosate Resistance by Engineering the Flavoenzyme Glycine Oxidase", JBC, Dec. 2009, 284(52):36415-36423.*
Database UniProt [Online], EMBL; Nov. 2, 2010 (Nov. 2, 2010), "FAD-dependent glycine oxidase", Database accession No. E0tzk8.
Boselli, A., et al., "Glycine oxidase from Bacillus subtilis; Role of Histidine 244 and Methionine 261," Biochimie 2007;89:1372-1380.
Supplementary European Search Report for European Patent App. No. 14773823.1 (Oct. 28, 2016).
International Search Report and Written Opinion for PCT Patent App. No. PCT/JP2014/059353 (dated Jul. 1, 2014) with English translation of the Search Report.
Martinez-Martinez, I., et al., "Implication of a mutation in the flavin binding site on the specific activity and substrate specificity of glycine oxidase from Bacillus subtilis produced by directed evolution," J. Biotechnol. 2008;133(1):1-8.
Pedotti, M., et al., "Glyphosate resistance by engineering the flavoenzyme glycine oxidase," J. Biol. Chem. 2009;284(52):36415-36423.
Katsurayama, A., et al., "Development of a Glycine Sensor Using Glycine Oxidase," Chemical Sensors, Sep. 27, 2013, 29, Supplement B, pp. 1-3.
Felig, P., et al., "Plasma Amino Acid Levels and Insulin Secretion in Obesity," N. Engl. J. Med. 1969;281:811-816.
Guerrieri, A., et al., "The kinetic and analytical behaviours of an L-lysine amperometric biosensor based on lysine oxidase immobilised onto a platinum electrode by co-crosslinking," Sens. Actuators B 2007;126:424-430.
Olschewski, H., et al., "Screen-printed enzyme sensors for L-lysine determination," Enzyme Microb. Technol. 2000;26:537-543.
Endo, H., et al., "Optical enzyme sensor for determining L-lysine content using L-lysine oxidase from the rockfish Sebastes schlegeli," Anal. Bioanal. Chem. 2008;391:1255-1261.
Caldinelli, L., et al., "FAD binding in glycine oxidase from Bacillus subtilis," Biochimie 2009;91:1499-1508.
Carpenter, S. E., et al., "An enzyme-coupled assay for glyoxylic acid," Anal. Biochem. 2003;323:242-246.

\* cited by examiner

*Primary Examiner* — Suzanne M Noakes
(74) *Attorney, Agent, or Firm* — Cermak Nakajima & McGowan LLP; Shelly Guest Cermak

(57) ABSTRACT

The present invention provides a novel enzyme and methods of using the enzyme for measuring glycine concentration. Specifically, the present invention provides an enzyme in which at least one amino acid residue is mutated so as to improve a property of a glycine oxidase which is associated with the measurement of glycine (e.g., activity of glycine oxidase for glycine, thermal stability of glycine oxidase, and substrate specificity of glycine oxidase for glycine,); and a method of analyzing glycine, that includes measuring glycine contained in a test sample using the modified enzyme; and the like.

13 Claims, 5 Drawing Sheets

SEQUENCE LISTING

<160> NUMBER OF SEQ ID NOS: 6

<210> SEQ ID NO 1
<211> LENGTH: 1107
<212> TYPE: DNA
<213> ORGANISM: Bacillus subtilis

<400> SEQUENCE: 1

```
atgaaaaggc attatgaagc agtggtgatt ggaggcggaa ttatcggttc cgcaattgct    60
tattatttgg caaaggaaaa caaaaacacc gcattgtttg aaagcggaac aatgggcggc   120
agaacgacaa gtgccgctgc cggaatgctg ggcgcccatg ccgaatgcga ggaacgtgac   180 gcgtttttg atttcgctat gcacagtcag cgtctgtaca aaggtcttgg agaagagctt   240
tatgcattat ccggtgtgga tatcaggcag cataacggcg gtatgtttaa gcttgcattt   300
tctgaagaag atgtgctgca gctgagacag atggacgatt tggactctgt cagctggtat   360
tcaaaagaag aggtgttaga aaaagagccg tatgcgtctg gtgacatctt tggtgcatct   420
tttattcagg atgatgtgca tgtggagcct tattttgttt gcaaggcata tgtgaaagca   480
gcaaaaatgc ttggggcgga gatttttgag catacgcccg tcctgcatgt cgaacgtgac   540
ggtgaagccc tgttcatcaa gacccctagc ggagacgtat gggctaatca tgttgtcgtt   600
gccagcgggg tgtggagcgg aatgttttt aaacagcttg gactgaacaa tgcttttctc   660
cctgtaaaag gggagtgcct gtccgtttgg aatgatgata tcccgctgac aaaaacgctt   720
taccatgatc actgctatat cgtaccgaga aaaagcggaa gactggttgt cggcgcgaca   780
atgaagccgg gggactggag tgaaacaccg gatcttggcg gattggaatc tgttatgaaa   840
aaagcaaaaa cgatgctgcc ggctatacag aatatgaagg tggatcgttt tgggcggga   900 ctccgtccgg gaacaaagga tggaaaaccg tacatcggca gacatcctga ggacagccgt   960 atttatttg cggctggcca tttcagaaac gggatcctgc ttgctcccgc aacgggcgct  1020
ttgatcagtg atctcatcat gaataaagag gtcaaccaag actggctgca cgcattccga  1080
attgatcgca aggaggcggt tcagata                                      1107
```

<210> SEQ ID NO 2
<211> LENGTH: 369
<212> TYPE: PRT
<213> ORGANISM: Bacillus subtilis

<400> SEQUENCE: 2

Met Lys Arg His Tyr Glu Ala Val Val Ile Gly Gly Ile Ile Gly
1               5                   10                  15

Ser Ala Ile Ala Tyr Tyr Leu Ala Lys Glu Asn Lys Asn Thr Ala Leu
            20                  25                  30

Phe Glu Ser Gly Thr Met Gly Arg Thr Thr Ser Ala Ala Ala Gly
        35                  40                  45

Met Leu Gly Ala His Ala Glu Cys Glu Arg Asp Ala Phe Phe Asp
    50                  55                  60

Phe Ala Met His Ser Gln Arg Leu Tyr Lys Gly Leu Gly Glu Glu Leu
65                  70                  75                  80

Tyr Ala Leu Ser Gly Val Asp Ile Arg Gln His Asn Gly Gly Met Phe
                85                  90                  95

Lys Leu Ala Phe Ser Glu Glu Asp Val Leu Gln Leu Arg Gln Met Asp
                100                 105                 110

Asp Leu Asp Ser Val Ser Trp Tyr Ser Lys Glu Glu Val Leu Glu Lys
            115                 120                 125

Glu Pro Tyr Ala Ser Gly Asp Ile Phe Gly Ala Ser Phe Ile Gln Asp
    130                 135                 140

Asp Val His Val Glu Pro Tyr Phe Val Cys Lys Ala Tyr Val Lys Ala
145                 150                 155                 160

Ala Lys Met Leu Gly Ala Glu Ile Phe Glu His Thr Pro Val Leu His
                165                 170                 175

Val Glu Arg Asp Gly Glu Ala Leu Phe Ile Lys Thr Pro Ser Gly Asp
            180                 185                 190

Val Trp Ala Asn His Val Val Ala Ser Gly Val Trp Ser Gly Met
    195                 200                 205

Phe Phe Lys Gln Leu Gly Leu Asn Asn Ala Phe Leu Pro Val Lys Gly
210                 215                 220

Glu Cys Leu Ser Val Trp Asn Asp Asp Ile Pro Leu Thr Lys Thr Leu
225                 230                 235                 240

Tyr His Asp His Cys Tyr Ile Val Pro Arg Lys Ser Gly Arg Leu Val
                245                 250                 255

Val Gly Ala Thr Met Lys Pro Gly Asp Trp Ser Glu Thr Pro Asp Leu
            260                 265                 270

Gly Gly Leu Glu Ser Val Met Lys Lys Ala Lys Thr Met Leu Pro Ala
        275                 280                 285

Ile Gln Asn Met Lys Val Asp Arg Phe Trp Ala Gly Leu Arg Pro Gly
290                 295                 300

Thr Lys Asp Gly Lys Pro Tyr Ile Gly Arg His Pro Glu Asp Ser Arg
305                 310                 315                 320

Ile Leu Phe Ala Ala Gly His Phe Arg Asn Gly Ile Leu Leu Ala Pro
                325                 330                 335

Ala Thr Gly Ala Leu Ile Ser Asp Leu Ile Met Asn Lys Glu Val Asn
            340                 345                 350

Gln Asp Trp Leu His Ala Phe Arg Ile Asp Arg Lys Glu Ala Val Gln
        355                 360                 365

Ile

<210> SEQ ID NO 3
<211> LENGTH: 41
<212> TYPE: DNA
<213> ORGANISM: Artificial Sequence
<220> FEATURE:

```
<223> OTHER INFORMATION: Primer for amplifying a polynucleotide encoding
      glyoxydase gene

<400> SEQUENCE: 3
taattccatg gctaaaaggc attatgaagc agtggtgatt g                           41

<210> SEQ ID NO 4
<211> LENGTH: 35
<212> TYPE: DNA
<213> ORGANISM: Artificial Sequence
<220> FEATURE:
<223> OTHER INFORMATION: Primer for amplifying a polynucleotide encoding
      glyoxydase gene

<400> SEQUENCE: 4
taatactcga gtatctgaac cgcctccttg cgatc                                  35

<210> SEQ ID NO 5
<211> LENGTH: 42
<212> TYPE: DNA
<213> ORGANISM: Artificial Sequence
<220> FEATURE:
<223> OTHER INFORMATION: Primer for amplifying a polynucleotide encoding
      glyoxydase gene

<400> SEQUENCE: 5
taattgaatt catgaaaagg cattatgaag cagtggtgat tg                          42

<210> SEQ ID NO 6
<211> LENGTH: 35
<212> TYPE: DNA
<213> ORGANISM: Artificial Sequence
<220> FEATURE:
<223> OTHER INFORMATION: Primer for amplifying a polynucleotide encoding
      glyoxydase gene

<400> SEQUENCE: 6
taatatctag atcagtggtg gtggtggtgg tgctc                                  35
```

MODIFIED GLYCINE OXIDASE

This application is a Continuation of, and claims priority under 35 U.S.C. § 120 to, International Application No. PCT/JP2014/059353, filed Mar. 28, 2014, and claims priority therethrough under 35 U.S.C. § 119 to Japanese Patent Application No. 2013-073906, filed Mar. 29, 2013, the entireties of which are incorporated by reference herein. Also, the Sequence Listing filed electronically herewith is hereby incorporated by reference (File name: 2015-09-23T_US-537_Seq_List; File size: 6 KB; Date recorded: Sep. 23, 2015).

SUMMARY OF THE INVENTION

Field of the Invention

The present invention relates to a modified glycine oxidase, a method of analyzing glycine using the same, and the like.

Brief Description of the Related Art

It is known that amino acids are very important as constituents in living bodies and some amino acids can become indicators of certain health conditions. For example, a particular concentration of glycine in plasma was suggested to be associated with obesity (P. Felig, E. Marliss, G. F. Cahill Jr. (1969) N. Engl. J. Med. 281, 811-816.). Glycine is found naturally in various foods, and is also used as a food additive. Therefore, the measurement of amino acids, particularly glycine, can be significant in a wide range of fields such as biological investigation, health nutrition, medical treatment, and food manufacture.

Instruments such as an amino acid analyzer, high performance liquid chromatography (HPLC) or LC-MS are widely used in methods of analyzing amino acids, including glycine. However, these instruments are large, require a lot of space, and are expensive, and also require technical knowledge and proficiency for their maintenance and operation. Thus, introduction, maintenance, and utilization of such instruments can be very costly. Also, it takes a long time to analyze many specimens because it is necessary to sequentially analyze each specimen in principle. To solve these problems, methods have been developed for analyzing amino acids using an enzyme that catalyzes a specific reaction for a specific amino acid, and kits for measuring some amino acids are commercially available. A biosensor for electrochemically or optically measuring a specific amino acid utilizing an enzyme has been also reported (e.g., International Publication WO2005/075970, A. Guerrieri, T. R. I. Cataldi, R. Ciriello. (2007) Sens. Actuators B Chem. 126, 424-430, H. Olschewski, A. Erlenkotter, C. Zaborosch, G.-C. Chemnitius. (2000) Enzyme Microb. Technol. 26, 537-543, and H. Endo, Y. Hayashi, Y. Kitani, H. Ren, T. Hayashi, Y. Nagashima. (2008) Anal. Bioanal. Chem. 391, 1255-1261. Glycine oxidase is known as an enzyme that acts upon glycine (e.g., L. Caldinelli, M. Pedotti, L. Motteran, G. Molla, L. Pollegioni (2009) Biochimie 91, 1499-1508).

SUMMARY OF THE INVENTION

In the aforementioned amino acid measurement using an enzyme, the properties of an enzyme, such as activity, stability and substrate specificity, which are associated with the amino acid measurement should be excellent. In particular for the activity, when the objective amino acid concentration to be detected in a specimen is low, such as an amino acid in blood, high enzymatic activity is required. Utilization of glycine oxidase is promising for analyzing a glycine-containing specimen, but it has been problematic because glycine oxidases are known to be low in activity and stability (e.g., S. E. Carpenter, D. J. Merkler (2003) Anal. Biochem. 323, 242-246). Also, the substrate specificity has not been investigated for many types of amino acids. As described above, no enzyme capable of practically measuring glycine is available. Thus, neither a practical method of measuring glycine nor a kit and biosensor for measuring glycine using the enzyme has been previously reported.

A modified glycine oxidase has been developed that has improved properties, enabling the measurement of glycine concentration using only the modified enzyme.

It is an aspect of the present invention to provide a glycine oxidase enzyme comprising a mutation of at least one amino acid residue, wherein said mutation results in the improvement of one or more properties of said glycine oxidase which are associated with measurement of glycine as compared to said glycine oxidase that does not comprise said mutation, wherein the one or more properties are selected from the group consisting of:

(a) an activity of the glycine oxidase for glycine;
(b) a thermal stability of the glycine oxidase; and
(c) a substrate specificity of the glycine oxidase for glycine.

It is a further aspect of the present invention to provide the glycine oxidase enzyme as described above, wherein the mutation is selected from the group consisting of (a) a substitution of the first threonine in a TTS motif, (b) a substitution of serine in the TTS motif, (c) a substitution of cysteine in an HCY motif, (d) a substitution of leucine in an LRP motif, (e) a substitution of methionine in a GML motif, (f) a substitution of serine in an SG motif, (g) a substitution of glycine in a PGT motif, and (h) combinations thereof.

It is a further aspect of the present invention to provide the glycine oxidase enzyme as described above, wherein the first threonine in the TTS motif is substituted with alanine, serine, cysteine, or glycine.

It is a further aspect of the present invention to provide the glycine oxidase enzyme as described above, wherein serine in the TTS motif is substituted with lysine.

It is a further aspect of the present invention to provide the glycine oxidase enzyme as described above, wherein cysteine in the HCY motif is substituted with alanine, aspartic acid, glycine, histidine, asparagine, tryptophan, tyrosine, or serine.

It is a further aspect of the present invention to provide the glycine oxidase enzyme as described above, wherein leucine in the LRP motif is substituted with isoleucine, valine, cysteine, threonine, or proline.

It is a further aspect of the present invention to provide the glycine oxidase enzyme as described above, wherein methionine in the GML motif is substituted with isoleucine.

It is a further aspect of the present invention to provide the glycine oxidase enzyme as described above, wherein serine in the SG motif is substituted with arginine.

It is a further aspect of the present invention to provide the glycine oxidase enzyme as described above, wherein glycine in the PGT motif is substituted with tyrosine or glutamine.

It is a further aspect of the present invention to provide the glycine oxidase enzyme as described above, wherein the glycine oxidase is derived from a bacteria of the genus *Bacillus*.

It is a further aspect of the present invention to provide the glycine oxidase enzyme as described above, wherein said glycine oxidase that does not comprise said mutation has the amino acid sequence of SEQ ID NO: 2; and (i) wherein the substitution of first threonine in the TTS motif is alanine, serine, cysteine, or glycine;
(ii) wherein the substitution of serine in the TTS motif is lysine;
(iii) wherein the substitution of cysteine in the HCY motif is alanine, aspartic acid, glycine, histidine, asparagine, tryptophan, tyrosine, or serine;
(iv) wherein the substitution of leucine in the LRP motif is isoleucine, valine, cysteine, threonine, or proline;
(v) wherein the substitution of methionine in the GML motif is isoleucine;
(vi) wherein the substitution of serine in the SG motif is arginine; and
(vii) wherein the substitution of glycine in the PGT motif is tyrosine or glutamine wherein the glycine oxidase enzyme may have supplemental mutations.

It is a further aspect of the present invention to provide a method of analyzing glycine comprising: (A) obtaining a test sample, and measuring glycine in the test sample using the glycine oxidase enzyme as described above.

It is a further aspect of the present invention to provide the method as described above, wherein said measuring comprises additionally using 4-aminoantipyrine, phenol, and peroxidase.

It is a further aspect of the present invention to provide a method of producing glyoxylic acid comprising forming the glyoxylic acid from glycine using the glycine oxidase enzyme as described above.

It is a further aspect of the present invention to provide a polynucleotide encoding the glycine oxidase enzyme as described above.

It is a further aspect of the present invention to provide an expression vector comprising the polynucleotide as described above.

It is a further aspect of the present invention to provide a transformant comprising the expression vector of as described above.

It is a further aspect of the present invention to provide a method of producing a glycine oxidase enzyme comprising using the transformant of as described above.

It is a further aspect of the present invention to provide a kit for analyzing glycine comprising the glycine oxidase enzyme as described above.

It is a further aspect of the present invention to provide the kit for analyzing glycine as described above, further comprising a component selected from the group consisting of a buffer solution, a reagent for detecting hydrogen peroxide, a reagent for detecting ammonia, a reagent for detecting glyoxylic acid, and combinations thereof.

It is a further aspect of the present invention to provide a detection system for analyzing glycine comprising (a) a device, and (b) the glycine oxidase enzyme as described above.

It is a further aspect of the present invention to provide the detection system for analyzing glycine as described above, further comprising a component selected from the group consisting of a buffer solution, a reagent for detecting hydrogen peroxide, a reagent for detecting ammonia, a reagent for detecting glyoxylic acid, and combinations thereof; and wherein the device is a microchannel chip.

It is a further aspect of the present invention to provide an enzyme sensor for analyzing glycine comprising (a) an electrode for detection, and (b) the glycine oxidase enzyme as described above, wherein said glycine oxidase is immobilized or retained on the electrode for detection.

The modified glycine oxidase enzyme as described herein is useful for rapid and highly sensitive measurement of glycine and/or production of glyoxylic acid because its activity for glycine is enhanced. The modified glycine oxidase enzyme also has excellent stability because it is excellent in thermal stability in an aqueous solution. Therefore the modified glycine oxidase enzyme is useful particularly as a liquid reagent. Further, the modified glycine oxidase enzyme can measure glycine specifically because it is excellent in substrate specificity for glycine. The analysis method as described herein is useful in a wide range of fields such as biological investigation, health nutrition, medical treatment and food manufacture.

DETAILED DESCRIPTION OF THE INVENTION

Figure 1:
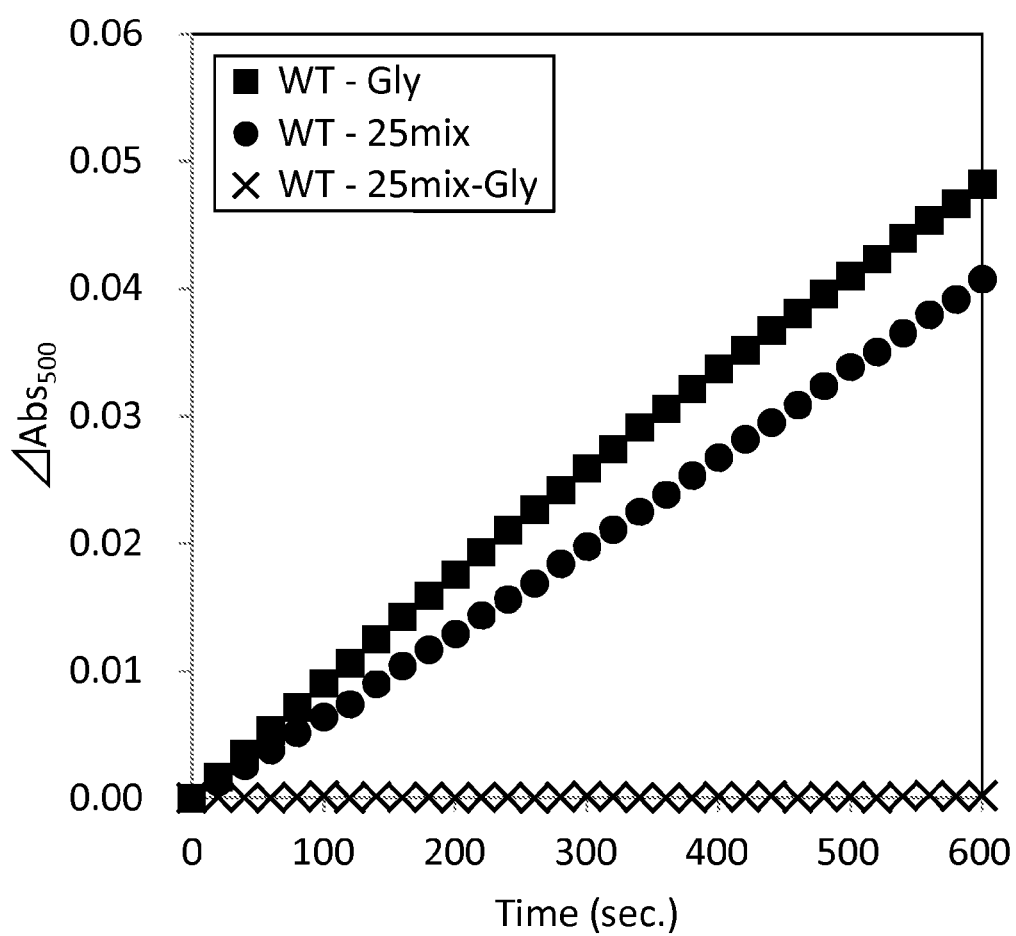
FIG. 1 shows substrate specificity of each wild-type glycine oxidase for glycine. (1) Gly: 1 mM glycine, (2) 25 mix: mixed solution containing standard 20 amino acids, cystine, taurine, citrulline, ornithine and α-aminobutyric acid each at 1 mM, and (3) 25 mix-Gly: mixed solution subtracting Gly from the 25 mix (the same shall apply hereinafter).

The present invention provides a modified enzyme that is able to measure glycine in a highly specific and sensitive manner. The modified enzyme has an activity of glycine oxidase and is modified so that at least one amino acid residue is mutated so as to improve a property of the glycine oxidase, which is associated with measurement of glycine.

Examples of the mutation of the amino acid residue may include substitution, deletion, addition and insertion, and substitution is preferred particular example.

The amino acid residue to be mutated can be L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), L-lysine (K), or glycine (G), all of which are naturally occurring L-α-amino acids. When the mutation is substitution, addition or insertion, the amino acid residue to be substituted, added or inserted can be the same as the amino acid residue to be mutated as described above. Hereinafter, L and a are sometimes skipped in the description of amino acids.

Glycine oxidase (glyoxidase: sometimes abbreviated as GlyOX) is an oxidoreductase that catalyzes the following reaction (EC 1.4.3.19).

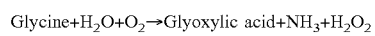

Glycine+$H_2O$+$O_2$→Glyoxylic acid+$NH_3$+$H_2O_2$

The glycine oxidase enzyme can be derived from many organisms and microorganisms, such as bacteria, actinomycetes and fungi, as well as insects, fishes, animals and plants.

Examples of the glycine oxidase may include enzymes derived from organisms belonging to the genus Bacillus and genera related thereto. Examples of the genera related to the genus Bacillus may include the genus Geobacillus, the genus Paenibacillus and the genus Oceanobacillus. The genera related to the genus Bacillus belong to Bacillaceae, as is similar to the genus Bacillus.

Examples of the microorganisms belonging to the genus Bacillus and the genera related thereto may include Bacillus aerophilus, Bacillus cereus, Bacillus macauensis, Bacillus pumilus, Bacillus subtilis, Bacillus sphaericus, Bacillus cereus, Bacillus licheniformis, Bacillus sp., Geobacillus stearothermophilus, and Geobacillus kaustophilus, and the like.

The position at which a mutation can be introduced in the glycine oxidase can be an amino acid residue located in close proximity to an active center of the glycine oxidase. Three-dimensional structure analysis has been reported for glycine oxidase derived from Bacillus subtilis (e.g., see PDB ID: 1NG3, 1NG4, 1RYI, 3IF9). A person skilled in the art can align the amino acid sequence of the glycine oxidase derived from Bacillus subtilis with an amino acid sequence of another glycine oxidase and thus can easily determine an amino acid residue located in close proximity to an active center of the glycine oxidase derived from organisms other than Bacillus subtilis.

An example of a mutation that can be made in the glycine oxidase to improve a property which is associated with the measurement of glycine includes a substitution of the first threonine (T) and/or serine (S) in a TTS motif in the amino acid sequence of a wild-type glycine oxidase. The TTS motif is composed of three consecutive amino acid residues of threonine (T)-threonine (T)-serine (S). The threonine residue at the C terminus of the TTS motif is sometimes referred to as the first threonine, and a threonine residue at central position of the TTS motif is sometimes referred to as the second threonine. The position of the TTS motif in the amino acid sequence of the wild-type glycine oxidase may be different depending on an origin of the enzyme. However, a person skilled in the art can appropriately determine the position of the TTS motif in the amino acid sequence of the wild-type glycine oxidase, and thus can specify positions of first threonine (T) and serine (S) to be substituted. Generally, in the amino acid sequence of the wild-type glycine oxidase, the TTS motif is located within an amino acid region from positions 42 to 44 and the first threonine (T) and the serine (S) are located at positions 42 and 44, respectively (see, e.g., Table 1).

TABLE 1

Position of first threonine (T) in TTS motif in glycine oxidase

| Glycine oxidase | Position TTS motif | 1st Thr | Accession No or SEQ ID NO |
|---|---|---|---|
| Bacillus subtilis | 42-44 | 42 | SEQ ID NO: 2 |
| Bacillus pumilus | 42-44 | 42 | ZP_03053300.1 |
| Bacillus aerophilus | 42-44 | 42 | ZP_10165124.1 |
| Bacillus atrophaeus | 42-44 | 42 | YP_003972581.1 |
| Bacillus amyloliquefaciens | 42-44 | 42 | YP_005420412.1 |

Another example of a mutation that can be made in the glycine oxidase to improve a property of the glycine oxidase which is associated with the measurement of glycine is the substitution of cysteine (C) in an HCY motif in an amino acid sequence of a wild-type glycine oxidase. The HCY motif is composed of three consecutive amino acid residues of histidine (H)-cysteine (C)-tyrosine (Y). The position of the HCY motif in the amino acid sequence of the wild-type glycine oxidase may be different depending on the origin of the enzyme. However, a person skilled in the art can appropriately determine the position of the HCY motif in the amino acid sequence of the wild-type glycine oxidase, and thus can determine the position of cysteine (C) to be substituted. Generally, in the amino acid sequence of the wild-type glycine oxidase, the HCY motif is located within an amino acid region from positions 244 to 252 and cysteine (C) is located at position from 245 to 251 (see, e.g., Table 2). The modified enzyme may further have the above substitution of first threonine (T) in the TTS motif in addition to the substitution of cysteine (C) in the HCY motif as the mutations to improve the property of the glycine oxidase which is associated with the measurement of glycine.

TABLE 2

Position of cysteine (C) in HCY motif in glycine oxidase

| Glycine oxidase | Position HCY motif | Cys | Accession No or SEQ ID NO |
|---|---|---|---|
| Bacillus subtilis | 244-246 | 245 | SEQ ID NO: 2 |
| Bacillus pumilus | 245-247 | 246 | ZP_03053300.1 |
| Bacillus aerophilus | 245-247 | 246 | ZP_10165124.1 |
| Bacillus macauensis | 250-252 | 251 | ZP_10322181.1 |
| Bacillus atrophaeus | 244-246 | 245 | YP_003972581.1 |
| Bacillus amyloliquefaciens | 244-246 | 245 | YP_005420412.1 |
| Bacillus licheniformis | 244-246 | 245 | YP_078461.1 |

Another example of a mutation that can be made in the glycine oxidase to improve a property of the glycine oxidase which is associated with the measurement of glycine is the substitution of leucine (L) in an LRP motif in an amino acid sequence of the wild-type glycine oxidase. The LRP motif is composed of three consecutive amino acid residues of leucine (L)-arginine (R)-proline (P). The position of the LRP motif in the amino acid sequence of the wild-type glycine oxidase may be different depending on the origin of the enzyme. However, a person skilled in the art can appropriately determine the position of the LRP motif in the amino acid sequence of the wild-type glycine oxidase, and thus can determine the position of leucine (L) to be substituted. Generally, in the amino acid sequence of the wild-type glycine oxidase, the LRP motif is located within an amino acid region from positions 294 to 316 and leucine (L) is located at position from 294 to 314 (see, e.g., Table 3). The modified glycine oxidase enzyme may further have the above substitution of first threonine (T) in the TTS motif and/or the above substitution of cysteine (C) in the HCY motif in addition to the substitution of leucine (L) in the LRP motif as the mutations to improve the property of the glycine oxidase which is associated with the measurement of glycine.

TABLE 3

Position of leucine (Leu) in LRP motif in glycine oxidase

| Glycine oxidase | Position LRP motif | Leu | Accession No or SEQ ID NO |
|---|---|---|---|
| Bacillus subtilis | 301-303 | 301 | SEQ ID NO: 2 |
| Bacillus pumilus | 302-304 | 302 | ZP_03053300.1 |
| Bacillus aerophilus | 302-304 | 302 | ZP_10165124.1 |
| Bacillus cereus | 307-309 | 307 | ZP_04243747.1 |

TABLE 3-continued

Position of leucine (Leu) in LRP motif in glycine oxidase

| Glycine oxidase | Position LRP motif | Leu | Accession No or SEQ ID NO |
|---|---|---|---|
| Bacillus atrophaeus | 301-303 | 301 | YP_003972581.1 |
| Bacillus amyloliquefaciens | 301-303 | 301 | YP_005420412.1 |
| Bacillus anthracis | 307-309 | 307 | ZP_02899039.1 |
| Bacillus thuringiensis | 307-309 | 307 | YP_005564450.1 |
| Bacillus pseudomycoides | 294-296 | 294 | ZP_04149837.1 |
| Bacillus mycoides | 294-296 | 294 | ZP_04155703.1 |
| Bacillus licheniformis | 301-303 | 301 | YP_078461.1 |
| Bacillus tusciae | 307-309 | 307 | YP_003588409.1 |
| Paenibacillus polymyxa | 314-316 | 314 | YP_003947104.1 |
| Alicyclobacillus acidocaldarius | 306-308 | 306 | YP_005519187.1 |
| Brevibacillus brevis | 305-307 | 305 | YP_002770374.1 |
| Paenibacillus mucilaginosus | 313-315 | 313 | YP_006188673.1 |
| Paenibacillus terrae | 314-316 | 314 | YP_005077007.1 |

Another example of a mutation that can be made in the glycine oxidase to improve a property of the glycine oxidase which is associated with the measurement of glycine is the substitution of methionine (M) in a GML motif in the amino acid sequence of the wild-type glycine oxidase. The GML motif is composed of three consecutive amino acid residues of glycine (G)-methionine (M)-leucine (L). The position of the GML motif in the amino acid sequence of the wild-type glycine oxidase may be different depending on the origin of the enzyme. However, a person skilled in the art can appropriately determine the position of the GML motif in the amino acid sequence of the wild-type glycine oxidase, and thus can determine the position of methionine (M) to be substituted. Generally, in the amino acid sequence of the wild-type glycine oxidase, the GML motif is located within an amino acid region from positions 45 to 59 and methionine (M) is located at position from 46 to 58 (e.g., Table 4). The modified glycine oxidase enzyme may further have the above substitutions of first threonine (T) and serine (S) in the TTS motif and/or the above substitution of cysteine (C) in the HCY motif and/or the above substitution of leucine (L) in the LRP motif in addition to the substitution of methionine (M) in the GML motif as the mutations to improve the property of the glycine oxidase which is associated with the measurement of glycine.

TABLE 4

Position of methionine (M) in GML motif in glycine oxidase

| Glycine oxidase | Position GML motif | Met | Accession No or SEQ ID NO |
|---|---|---|---|
| Bacillus subtilis | 48-50 | 49 | SEQ ID NO: 2 |
| Bacillus pumilus | 48-50 | 49 | ZP_03053300.1 |
| Bacillus sp. | 48-50 | 49 | ZP_10165124.1 |
| Bacillus macauensis | 48-50 | 49 | ZP_10322181.1 |
| Bacillus atrophaeus | 48-50 | 49 | YP_003972581.1 |
| Bacillus amyloliquefaciens | 48-50 | 49 | YP_005420412.1 |
| Bacillus licheniformis | 48-50 | 49 | YP_078461.1 |
| Kyrpidia tusciae | 49-51 | 50 | YP_003588409.1 |
| Paenibacillus polymyxa | 57-59 | 58 | YP_003947104.1 |
| Alicyclobacillus acidocaldarius | 47-49 | 48 | YP_005519187.1 |
| Brevibacillus brevis | 45-47 | 46 | YP_002770374.1 |
| Paenibacillus mucilaginosus | 56-58 | 57 | YP_006188673.1 |
| Paenibacillus terrae | 57-59 | 58 | YP_005077007.1 |

Another example of a mutation that can be made in the glycine oxidase to improve a property of the glycine oxidase which is associated with the measurement of glycine is the substitution of serine (S) in an SG motif in the amino acid sequence of the wild-type glycine oxidase. The SG motif is composed of consecutive two amino acid residues of serine (S)-glycine (G). The position of the SG motif in the amino acid sequence of the wild-type glycine oxidase may be different depending on the origin of the enzyme. However, a person skilled in the art can appropriately determine the position of the SG motif in the amino acid sequence of the wild-type glycine oxidase, and thus can determine the position of serine (S) to be substituted. Generally, in the amino acid sequence of the wild-type glycine oxidase, the SG motif is located within an amino acid region from positions 190 to 204 and serine (S) is located at position from 190 to 203 (see, e.g., Table 5). The modified glycine oxidase enzyme may further have the above substitutions of first threonine (T) and serine (S) in the TTS motif and/or the above substitution of cysteine (C) in the HCY motif and/or the above substitution of leucine (L) in the LRP motif and/or the above substitution of methionine (M) in the GML motif in addition to the substitution of serine (S) in the SG motif as the mutations to improve the property of the glycine oxidase which is associated with the measurement of glycine.

TABLE 5

Position of serine (S) in SG motif in glycine oxidase

| Glycine oxidase | Position SG motif | Ser | Accession No or SEQ ID NO |
|---|---|---|---|
| Bacillus subtilis | 190-191 | 190 | SEQ ID NO: 2 |
| Bacillus polymyxa | 203-204 | 203 | YP_003947104.1 |
| Brevibacillus brevis | 194-195 | 194 | YP_002770374.1 |
| Paenibacillus terrae | 203-204 | 203 | YP_005077007.1 |

Another example of a mutation that can be made in the glycine oxidase to improve a property of the glycine oxidase which is associated with the measurement of glycine is the substitution of glycine (G) in a PGT motif in the amino acid sequence of the wild-type glycine oxidase. The PGT motif is composed of consecutive three amino acid residues of proline (P)-glycine (G)-threonine (T). The position of the PGT motif in the amino acid sequence of the wild-type glycine oxidase may be different depending on the origin of the enzyme. However, a person skilled in the art can appropriately determine the position of the PGT motif in the amino acid sequence of the wild-type glycine oxidase, and thus can determine a position of glycine (G) to be substituted. Generally, in the amino acid sequence of the wild-type glycine oxidase, the PGT motif is located within an amino acid region from positions 303 to 317 and glycine (G) is located at position from 304 to 316 (see, e.g., Table 6). The modified glycine oxidase enzyme may further have the above substitutions of first threonine (T) and serine (S) in the TTS motif and/or the above substitution of cysteine (C) in the HCY motif and/or the above substitution of leucine (L) in the LRP motif and/or the above substitution of methionine (M) in the GML motif and/or the above substitution of serine (S) in the SG motif in addition to the substitution of glycine (G) in the PGT motif as the mutations to improve the property of the glycine oxidase which is associated with the measurement of glycine.

TABLE 6

Position of glycine (G) in PGT motif in glycine oxidase

| Glycine oxidase | Position PGT motif | Gly | Accession No or SEQ ID NO |
|---|---|---|---|
| Bacillus subtilis | 303-305 | 304 | SEQ ID NO: 2 |
| Bacillus atrophaeus | 303-305 | 304 | YP_003972581.1 |
| Bacillus amyloliquefaciens | 303-305 | 304 | YP_005420412.1 |
| Paenibacillus mucilaginosus | 315-317 | 316 | YP_006188673.1 |

The glycine oxidase enzyme can be produced by introducing a mutation or mutations into a wild-type enzyme having one or more motifs selected from the aforementioned six motifs. The wild-type enzyme may have 2 motifs, 3 motifs, 4 motifs, 5 motifs, or 6 motifs selected from the aforementioned 6 motifs.

The properties of the glycine oxidase which are associated with the measurement of glycine may include the following:

(a) an activity of the glycine oxidase for glycine;
(b) a thermal stability of the glycine oxidase; and
(c) a substrate specificity of the glycine oxidase for glycine.

The modified glycine oxidase enzyme may have only one of the aforementioned properties, or may have two or three of the aforementioned properties in combination.

For the first threonine (T) in the TTS motif, examples of the mutation to improve at least one property selected from the properties (a) to (c) (a single mutation alone or in combination with another mutation or mutations) may include a substitution with alanine (A), serine (S), cysteine (C) or glycine (G).

For serine (S) in the TTS motif, examples of the mutation to improve at least one property selected from the properties (a) to (c) (a single mutation alone or in combination with another mutation or mutations) may include a substitution with lysine (K).

For cysteine (C) in the HCY motif, examples of the mutation to improve at least one property selected from the properties (a) to (c) (a single mutation alone or in combination with another mutation or mutations) may include a substitution with alanine (A), aspartic acid (D), glycine (G), histidine (H), asparagine (N), tryptophan (W), tyrosine (Y) or serine (S).

For leucine (L) in the LRP motif, examples of the mutation to improve at least one property selected from the properties (a) to (c) (a single mutation alone or in combination with another mutation or mutations) may include a substitution with isoleucine (I), valine (V), cysteine (C), threonine (T), or proline (P).

For methionine (M) in the GML motif, examples of the mutation to improve at least one property selected from the properties (a) to (c) (a single mutation alone or in combination with another mutation or mutations) may include a substitution with isoleucine (I).

For serine (S) in the SG motif, examples of the mutation to improve at least one property selected from the properties (a) to (c) (a single mutation alone or in combination with another mutation or mutations) may include a substitution with arginine (R).

For glycine (G) in the PGT motif, examples of the mutation to improve at least one property selected from the properties (a) to (c) (a single mutation alone or in combination with another mutation or mutations) may include a substitution with tyrosine (Y) or glutamine (Q).

In one embodiment, the activity of the glycine oxidase for glycine is improved as the property of the glycine oxidase which is associated with the measurement of glycine. The improvement of the activity of the glycine oxidase for glycine means that the activity of the modified enzyme for glycine is enhanced relative to the activity of the wild-type or non-modified enzyme for the same. Specifically, the improvement of the activity of the glycine oxidase for glycine can be accomplished in the case where the activity of the modified glycine oxidase for glycine at predetermined concentration (either at low or high concentration) is higher than 100 when the activity of the wild-type glycine oxidase for glycine is regarded as 100 at the same concentration. Such a modified enzyme enables rapid measurement of glycine with high sensitivity, and consequently is useful for the measurement of glycine. A level of the enhancement of the activity of the modified enzyme can be 1.3 fold or more, 1.5 fold or more, 1.7 fold or more, or 2.0 fold or more relative to the activity of the wild-type enzyme. Examples of the mutation in the modified glycine oxidase enzyme having 1.3 fold or more enhancement of the activity relative to the wild-type enzyme may be (1) the substitution of first threonine (T) in the TTS motif with the following amino acid residue, the substitution of cysteine (C) in the HCY motif with the following amino acid residue, the substitution of leucine (L) in the LRP motif with the following amino acid residue, or a combination thereof, which is suitable for the improvement of the activity.

(1) Substitutions suitable for improvement of activity
(1-1) Amino acid residues after substitution of first threonine (T) in TTS motif
Alanine (A), serine (S), cysteine (C) or glycine (G)
(1-2) Amino acid residues after substitution of serine (S) in TTS motif
Lysine (K)
(1-3) Amino acid residues after substitution of cysteine (C) in HCY motif
Serine (S)
(1-4) Amino acid residues after substitution of leucine (L) in LRP motif
Isoleucine (I), valine (V), cysteine (C), or threonine (T)
(1-5) For glycine (G) in the PGT motif, examples of the mutation to improve at least one property selected from the properties (a) to (c) (a single mutation alone or in combination with another mutation or mutations) may include a substitution with glutamine (Q).

In another embodiment, the thermal stability of the glycine oxidase can be improved as the property of the glycine oxidase which is associated with the measurement of glycine. The improvement of the thermal stability of the glycine oxidase can mean that the thermal stability of the modified enzyme is further enhanced relative to that of the wild-type or non-modified enzyme. Specifically, the improvement of the thermal stability of the glycine oxidase can be accomplished in the case where a remaining activity of the modified enzyme is higher than that of the wild-type enzyme when the enzyme is treated in an aqueous solution at predetermined high temperature (e.g., any temperature of 40° C., 50° C. or 60° C.) for a predetermined period of time (e.g., one hour). A thermal stability test of the glycine oxidase in the aqueous solution can have significance as an acceleration test for evaluating the stability (particularly liquid stability) of the glycine oxidase. Therefore, when the thermal stability of the modified enzyme in the aqueous solution is high, the stability (particularly liquid stability) of the modified enzyme also tends to be high. An enzyme having high liquid stability can be stored in a liquid form for a long period of time, and thus, such a modified enzyme is useful as a liquid reagent for the measurement of glycine. The level of the enhancement of the thermal stability of the modified enzyme can be 1.1 fold or more, or 1.2 fold or more, relative to that of the wild-type enzyme. Examples of the mutation in the modified enzyme having 1.1 fold or more enhanced thermal stability relative to the wild-type enzyme may be (2) the substitution of cysteine (C) in the HCY motif with the following amino acid residue, which is suitable for the improvement of the thermal stability.

(2) Substitutions suitable for improvement of thermal stability (2-1) Amino acid residues after substitution of first threonine (T) in TTS motif Alanine (A), serine (S) or glycine (G)

(2-2) Amino acid residues after substitution of serine (S) in TTS motif

Lysine (K)

(2-3) Amino acid residues after substitution of cysteine (C) in HCY motif

Alanine (A), aspartic acid (D), glycine (G), histidine (H), asparagine (N), tryptophan (W), tyrosine (Y) or serine (S)

(2-4) Amino acid residues after substitution of leucine (L) in LRP motif

Isoleucine (I), valine (V), proline (P), or cysteine (C)

(2-5) For methionine (M) in the GML motif, examples of the mutation to improve at least one property selected from the properties (a) to (c) (a single mutation alone or in combination with another mutation or mutations) may include a substitution with isoleucine (I).

(2-6) For serine (S) in the SG motif, examples of the mutation to improve at least one property selected from the properties (a) to (c) (a single mutation alone or in combination with another mutation or mutations) may include a substitution with arginine (R).

(2-7) For glycine (G) in the PGT motif, examples of the mutation to improve at least one property selected from the properties (a) to (c) (a single mutation alone or in combination with another mutation or mutations) may include a substitution with tyrosine (Y) or glutamine (Q).

In still another embodiment, the substrate specificity of the glycine oxidase for glycine is improved as the property of the glycine oxidase which is associated with the measurement of glycine. The improvement of the substrate specificity of the glycine oxidase for glycine means that a reactivity of the modified enzyme for glycine is further enhanced compared with that of the wild-type enzyme, and in other words, means that the reactivity of the modified enzyme for amino acids other than glycine is reduced. Examples of the amino acids other than glycine may include L-α-amino acids other than glycine. Specifically, examples of the amino acids other than glycine may include 19 L-α-amino acids other than glycine, and cystine, taurine, citrulline, ornithine and α-aminobutyric acid, which compose proteins. The mutation of the modified enzyme, in which the substrate specificity of the glycine oxidase for glycine is improved can be, for example, the substitution of the first threonine (T) in the TTS motif with the following amino acids residue, the substitution of cysteine (C) in the HCY motif with the following amino acids residue, the substitution of leucine (L) in the LRP motif with the following amino acids residue, or a combination thereof.

(3) Substitutions suitable for improvement of substrate specificity (3-1) Amino acid residue after substitution of first threonine (T) in TTS motif Alanine (A)

(3-2) Amino acid residue after substitution of cysteine (C) in HCY motif

Serine (S)

(3-3) Amino acid residue after substitution of leucine (L) in LRP motif

Valine (V)

The modified glycine oxidase enzyme may also have another peptide component, such as a tag moiety, at the C-terminus or N-terminus. Examples of the other peptide component that can be added to the modified enzyme may include peptide components that make purification of the objective protein easy, such as a tag moiety such as a histidine tag and strep-tag II; proteins such as glutathione-S-transferase and maltose-binding protein commonly used for the purification of the objective protein, peptide components that enhance solubility of the objective protein (e.g., Nus-tag), peptide components that work as a chaperon (e.g., trigger factor), and peptide components as a protein or a domain of the protein having another function or a linker connecting them.

The modified glycine oxidase enzyme may also have supplemental mutations, such as substitutions, deletions, insertions, and/or additions, of one or several amino acid residues in an amino acid sequence of the glycine oxidase having the above mutation(s) as long as the aforementioned property is maintained. The number of the supplemental mutations can be, for example, 1 to 100, 1 to 50, 1 to 40, 1 to 30, 1 to 20, or 1 to 10, and including 1, 2, 3, 4, or 5. A person skilled in the art can appropriately make such a modified enzyme that maintains the aforementioned property. In the modified enzyme having the supplemental mutation or mutations, the level of the enhancement of the activity of the modified enzyme can be 1.3 fold or more, 1.5 fold or more, 1.7 fold or more, or 2.0 fold or more relative to the activity of the wild-type enzyme. Also in the modified enzyme having the supplemental mutation or mutations, the level of the enhancement of the thermal stability of the modified enzyme can be 1.1 fold or more, or 1.2 fold or more relative to that of the wild-type enzyme.

Therefore, the modified enzyme may be the following (i) or (ii):

(i) a protein having an amino acid sequence having a mutation or mutations (e.g., substitution) of one or more amino acid residues, such as the first threonine in the TTS motif, serine in the TTS motif, cysteine in the HCY motif, leucine in the LRP motif, methionine in the GML motif, serine in the SG motif, and/or glycine in the PGT motif in an amino acid sequence of the glycine oxidase, and having an improved property of the glycine oxidase which is associated with the measurement of glycine; or (ii) a protein having an amino acid sequence having a supplemental mutation of one or several amino acid residues in the amino acid sequence having a mutation or mutations (e.g., substitution) of one or more amino acids such as the first threonine in the TTS motif, serine in the TTS motif, cysteine in the HCY motif, leucine in the LRP motif, methionine in the GML motif, serine in the SG motif and glycine in the PGT motif in an amino acid sequence of the glycine oxidase, and retaining an improved property of the glycine oxidase which is associated with the measurement of glycine.

The modified enzyme may also be have an amino acid sequence having at least 90% or more sequence identity to the amino acid sequence of the (wild-type) glycine oxidase before its mutation because of having both the aforementioned mutation or mutations and the supplemental mutation or mutations. A percentage of the amino acid sequence identity may be preferably 92% or more, 95% or more, 97% or more, 98% or more, or 99% or more.

The identity between the amino acid sequences can be determined, for example, using algorithm BLAST by Karlin and Altschul (Pro. Natl. Acad. Sci. USA, 90, 5873 (1993)) and FASTA by Pearson (Methods Enzymol., 183, 63 (1990)). A program referred to as BLASTP has been developed based on this algorithm BLAST (see http://www.ncbi.nlm.nih.gov). Thus, the identity between the amino acid sequences may be calculated using these programs with default setting. Also, for example, a numerical value obtained by calculating similarity as a percentage using a full length polypeptide portion encoded in an ORF and using software GENETYX Ver. 7.09 with setting of Unit Size to Compare=2 from Genetyx Corporation employing Lipman-Pearson method may be used as the identity between the amino acid sequences. The lowest value among the values derived from these calculations may be employed as the identity between the amino acid sequences.

The position of an amino acid residue at which the supplemental mutation can be introduced in an amino acid sequence is apparent to a person skilled in the art. For example, the supplemental mutation can be introduced with reference to an alignment of the amino acid sequence. Specifically, a person skilled in the art can (1) compare amino acid sequences of a plurality of homologs, such as the amino acid sequence represented by SEQ ID NO:2 and an amino acid sequence of the other homolog, (2) demonstrate relatively conserved regions and relatively non-conserved regions, then (3) predict regions capable of playing a functionally important role and regions incapable of playing a functionally important role from the relatively conserved regions and the relatively non-conserved regions, respectively, and thus recognize the correlation between structure and function. The three-dimensional structure analysis has been reported for glycine oxidase as described above. Thus, a person skilled in the art can introduce the supplemental mutation based on the analysis result of the three-dimensional structure so as to enable the maintenance of the aforementioned property. The sites to which the supplemental mutations is introduced may be an amino acid residue other than the first threonine in the TTS motif, serine in the TTS motif, cysteine in the HCY motif, leucine in the LRP motif, methionine in the GML motif, serine in the SG motif and glycine in the PGT motif, and can be amino acid residues other than the amino acids residues in the TTS motif, the TTS motif, the HCY motif, the LRP motif, the GML motif, the SG motif and the PGT motif.

When the supplemental mutation of the amino acid residue is a substitution, such a substitution of the amino acid residue may be a conservative substitution. The term "conservative substitution" refers to substituting a given amino acid residue with an amino acid residue having a similar side chain. Families of the amino acid residues having the similar side chain are well-known in the art. Examples of such families may include amino acids having a basic side chain (e.g., lysine, arginine, histidine), amino acids having an acidic side chain (e.g., aspartic acid, glutamic acid), amino acids having an uncharged polar side chain (e.g., asparagine, glutamine, serine, threonine, tyrosine, cysteine), amino acids having a nonpolar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a side chain containing a hydroxyl (e.g., alcoholic, phenolic) group (e.g., serine, threonine, tyrosine), and amino acids having a sulfur-containing side chain (e.g., cysteine, methionine). In one example, the conservative substitution of the amino acid may be a substitution of aspartic acid with glutamic acid and vice versa, a substitution among arginine, lysine and histidine, a substitution of tryptophan with phenylalanine and vice versa, a substitution of phenylalanine with valine and vice versa, a substitution among leucine, isoleucine and alanine, and a substitution of glycine with alanine and vice versa.

The modified glycine oxidase enzyme can be prepared using a transformant, which is able to express the modified enzyme, a cell-free system, or the like. The transformant can be made, for example, by making an expression vector for the modified glycine oxidase enzyme and introducing this expression vector into a host.

The expression vector can include a polynucleotide (e.g., DNA, RNA) encoding the modified glycine oxidase enzyme. The expression vector can further include regions that encode a promoter, a terminator and a drug (e.g., tetracycline, ampicillin, kanamycin, hygromycin, phosphinothricin) resistant gene, in addition to the polynucleotide. The expression vector may be a plasmid or an integrative vector. The expression vector may also be a viral vector or a vector for a cell-free system. The expression vector may further include a polynucleotide encoding another peptide component that can be added to the modified glycine oxidase enzyme on the 3' or 5' terminal side of the polynucleotide. Examples of the polynucleotide encoding a peptide component may include a polynucleotide encoding the peptide component that makes the purification of an objective protein easy as described above, a polynucleotide encoding the peptide component that enhances solubility of the objective protein as described above, a polynucleotide encoding the peptide component that works as a chaperon, and a polynucleotide encoding the peptide component as a protein or a domain of the protein having another function or a linker connecting them. Various expression vectors that include the polynucleotide encoding the other peptide component are available. Therefore, such an expression vectors may be utilized for making the expression vector. For example, an expression vector that includes the polynucleotide encoding the peptide component that makes the purification of the objective protein easy (e.g., pET-15b, pET-51b, pET-41a, pMAL-p5G), an expression vector that includes the polynucleotide encoding the peptide component that enhances solubility of the objective protein (e.g., pET-50b), an expression vector that includes the polynucleotide encoding the peptide component that works as the chaperon (pCold TF), and an expression vector that includes the polynucleotide encoding the peptide component as the protein or the domain of the protein having another function or the linker connecting them can be utilized. In order to cleave the modified glycine oxidase enzyme from the other peptide component added thereto after the expression of a protein, the expression vector may include a region encoding a cleavage site by protease between the polynucleotide encoding the modified glycine oxidase enzyme and the polynucleotide encoding the other peptide component.

Various prokaryotic cells including cells from bacteria belonging to genera *Escherichia* (e.g., *Escherichia coli*), *Corynebacterium* (e.g., *Corynebacterium glutamicum*) and *Bacillus* (e.g., *Bacillus subtilis*), and various eukaryotic cells including cells from fungi belonging to genera *Saccharomyces* (e.g., *Saccharomyces cerevisiae*), *Pichia* (e.g., *Pichia stipitis*) and *Aspergillus* (e.g., *Aspergillus oryzae*) can be used as the host for expressing the modified glycine oxidase enzyme. A strain in which a certain gene has been deleted may be used as the host. Examples of the transformant may include transformants in which the vector is retained in its cytoplasm and transformants in which an objective gene is integrated into its genome.

The transformant can be cultured in a medium having a composition described later using a given culture apparatus (e.g., test tube, flask, jar fermenter). The culture conditions can appropriately be determined. Specifically, the culture temperature may be 10 to 37° C., the pH value may be 6.5 to 7.5, and the culture period may be 1 to 100 hours. The cultivation may also be carried out with managing a dissolved oxygen concentration. In this case, the dissolved oxygen concentration (DO value) may be used as an indicator for a control. The ventilation/stirring condition can be controlled so that a relative dissolved oxygen concentration, that is, the DO value, should not be below 1 to 10% for example, and preferably not below 3 to 8%, when the oxygen concentration in the air is 21%. The cultivation may be a batch cultivation or a fed-batch cultivation. In the case of the fed-batch cultivation, the cultivation can also be continued by sequentially adding continuously or discontinuously a solution as a sugar source and a solution containing phosphoric acid to the culture medium.

The host to be transformed is as described above, and specifically if Escherichia coli, the host can be Escherichia coli K12 subspecies Escherichia coli JM109 strain, DH5a strain, HB101 strain, BL21 (DE3) strain, and the like. Methods of performing the transformation and methods of selecting the transformant are described in Molecular Cloning: A Laboratory Manual, 3rd edition, Cold Spring Harbor press (2001/01/15), and the like. Hereinafter, a method of making transformed Escherichia coli and producing a predetermined enzyme using this will be described specifically by way of example only.

A promoter useful for producing a foreign protein in E. coli can generally be used as a promoter for expressing the polynucleotide. Examples thereof may include potent promoters such as a PhoA, PhoC, T7 promoter, a lac promoter, a trp promoter, a trc promoter, a tac promoter, PR and PL promoters of lambda phage, and a T5 promoter, and the PhoA, PhoC and lac promoters are particular examples. For example, pUC (e.g., pUC19, pUC18), pSTV, pBR (e.g., pBR322), pHSG (e.g., pHSG299, pHSG298, pHSG399, pHSG398), RSF (e.g., RSF1010), pACYC (e.g., pACYC177, pACYC184), pMW (e.g., pMW119, pMW118, pMW219, pMW218), pQE (e.g., pQE30) and derivatives thereof may be used as the vector. A vector from phage DNA may also be used as the other vector. Further, an expression vector that includes a promoter and can express an inserted DNA sequence may also be used. Preferably, the vector may be pUC, pSTV, or pMW.

Also, a terminator that is a transcription terminating sequence may be ligated downstream of the polynucleotide. Examples of such a terminator may include a T7 terminator, an fd phage terminator, a T4 terminator, a terminator of a tetracycline resistant gene, and a terminator of Escherichia coli trpA gene.

The vector for introducing the polynucleotide into Escherichia coli can be a so-called multicopy type, and examples thereof may include plasmids which have a replication origin from ColE1, such as pUC-based plasmids, pBR322-based plasmids or derivatives thereof. Here the "derivative" can mean those in which a modification such as substitution, deletion, insertion and/or addition of nucleotide (s) has been made to the plasmid.

In order to select the transformant, the vector can have a marker such as an ampicillin resistant gene. Expression vectors having a potent promoter are commercially available as such a plasmid (e.g., pUC-based (supplied from Takara Bio Inc.), pPROK-based (supplied from Clontech), pKK233-2-based (supplied from Clontech)).

The modified enzyme can be obtained by transforming Escherichia coli using the resulting expression vector and culturing this Escherichia coli.

Media such as M9/casamino acid medium and LB medium generally used for culturing Escherichia coli may be used as the medium. The medium may contain a predetermined carbon source, nitrogen source, and coenzyme (e.g., pyridoxine hydrochloride). Specifically, peptone, yeast extract, NaCl, glucose, MgSO$_4$, ammonium sulfate, potassium dihydrogen phosphate, ferric sulfate, manganese sulfate, and the like may be used. The cultivation conditions and production inducing conditions can be appropriately selected depending on the types of marker and promoter in the chosen vector and the chosen host, and the like.

The modified glycine oxidase enzyme can be recovered by the following methods. The modified enzyme can be obtained as a pulverized or lysed product by collecting the transformant and subsequently pulverizing (e.g., sonication or homogenization) or lysing (e.g., treatment with lysozyme) the microbial cells. The modified enzyme can be obtained by subjecting such a pulverized or lysed product to techniques such as extraction, precipitation, filtration, and column chromatography.

The present invention also provides a method of analyzing glycine. The analysis method includes obtaining a test sample and measuring glycine in the test sample using the modified enzyme as described herein.

The test sample is not particularly limited as long as the sample is suspected of containing glycine, and examples thereof may include biological samples (e.g., blood, urine, saliva, tear, and the like) and food and beverage (e.g., nutrient drinks and amino acid beverages). Glycine in the test sample may be at a low concentration (e.g., concentration less than 1 mM such as 1 µM or more and less than 1 mM) or a high concentration (concentration of 1 mM or more such as 1 mM or more and less than 1 M).

The analysis method is not particularly limited as long as glycine can be measured using the modified enzyme. The method may detect glyoxylic acid, or may detect NH$_3$ or H$_2$O$_2$ produced as by-products along with the formation of the glyoxylic acid. Alternatively, another reaction may be conjugated to detect a product of a conjugate reaction. Examples of such conjugate reactions may include the following conjugate reaction.

Glycine oxidation reaction: reaction catalyzed by glycine oxidase

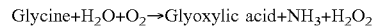

Conjugate reaction: reaction catalyzed by peroxidase

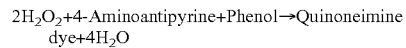

When the above conjugate reaction is utilized, the measurement of glycine can be carried out using 4-aminoantipyrine and phenol, and peroxidase in addition to the modified glycine oxidase enzyme. Specifically, glycine is measured by mixing a test sample with 4-aminoantipyrine and phenol, and peroxidase in an aqueous solution, such as a buffer, then subjecting the mixed sample to the above enzymatic reaction, and finally detecting an absorbance (about 500 nm) of quinoneimine dye. The measurement can be carried out qualitatively or quantitatively. The measurement may be carried out based on an endpoint method in which the measurement is performed until the entire substrates are reacted or based on a rating method (initial rate method). An amount of oxygen required for the oxidation reaction is very small, and the required amount of oxygen is covered with dissolved oxygen in a reaction system. Thus generally, it is not necessary to forcibly supply oxygen or a gas containing the oxygen to the reaction system.

The modified enzyme does not react with amino acids (e.g., L-α-amino acids) other than glycine or has a low reactivity therewith. Therefore, even when not only glycine but also other amino acids are present in a test sample, an amount of glycine in the test sample can specifically be evaluated by using the modified glycine oxidase enzyme.

The amount of glycine in the test sample can specifically be evaluated by using a hydrogen peroxide electrode using the modified enzyme.

Further, the present invention includes a kit for analyzing glycine including (A) the modified enzyme.

The kit can further include at least one of (B) a buffer solution or a buffer salt for a reaction, (C) a reagent for detecting hydrogen peroxide, (D) a reagent for detecting ammonia, and (E) a reagent for detecting glyoxylic acid.

(B) The buffer solution or the buffer salt for the reaction is used for keeping a pH value in a reaction solution suitable for an objective enzymatic reaction.

(C) The reagent for detecting hydrogen peroxide is used when hydrogen peroxide is detected, for example, by color development or fluorescence. Examples may include a combination of peroxidase with a color-producing agent that can become its substrate. Specific examples may include, but are not limited to a combination of horseradish peroxidase with 4-aminoantipyrine and phenol.

Examples of (D) the reagent for detecting ammonia may include an indophenol method combining phenol with hypochlorous acid.

Examples of (E) the reagent for detecting glyoxylic acid may include a combination of the reagents as described in S. E. Carpenter, D. J. Merkler (2003) Anal. Biochem. 323, 242-246.

The present invention also provides a detection system for the analysis of glycine that includes (a) a device and (b) the modified glycine oxidase enzyme.

The modified enzyme may be present as a unit that is independent from a microdevice capable of being supplied in the device upon use, or may previously be injected in, immobilized to or retained on the device. Preferably, the modified enzyme is provided in a form of previously being injected in, immobilized to or retained on the device. The modified enzyme is directly or indirectly immobilized to or retained on the device. For example, the microdevice such as a microchannel chip that includes a channel can suitably be used as the device.

The detection system for the analysis of glycine may further include (c) at least one constituent of the buffer solution or the buffer salt for the reaction, the reagent for detecting hydrogen peroxide, the reagent for detecting ammonia, and the reagent for detecting glyoxylic acid. The detection system for the analysis of glycine may be provided in a form in which the constituents (c) have been entirely accommodated in the device, or in a form in which the constituents (c) have been partially accommodated in the device and the remaining has not been accommodated in the device (e.g., a form of being accommodated in different containers). In this case, the constituent (c) that is not accommodated in the device may be used by injecting it into the device when a target substance is measured.

Examples of the device may include (1) a device that has a first section for preparing a mixed solution by mixing a sample with the constituents (c) and a second section for detecting glycine by contacting the prepared mixed solution with the modified glycine oxidase enzyme (device in which a step of mixing and a step of detection are carried out in the different section); (2) a device that has a section for mixing the sample and the constituents (c) with the modified glycine oxidase enzyme to detect glycine by the modified enzyme (device in which the step of mixing and the step of detection are carried out in the same section); and (3) a device that has a channel that enables mixing the sample and the constituents (c) (and the modified enzyme if necessary) and a section for detecting glycine by the modified glycine oxidase enzyme of the present invention (device in which when the sample is injected in an inlet of the device, the sample is sent through the channel to automatically mix the sample and the like, and glycine in the resulting mixed solution is automatically detected in the detection section). The device (3), in particular, the device (3) that is a form of the microchannel device is preferred in terms of automation. In the device (3), the modified enzyme may be provided in a sending solution that runs in the channel or may be provided in a form of being immobilized or retained to the detection section, and is preferably provided in the form of being immobilized or retained to the detection section.

The present invention also provides an enzyme sensor for analyzing glycine that includes (a) an electrode for detection and (b) the modified glycine oxidase enzyme immobilized or retained on the electrode for detection. The modified enzyme is immobilized or retained on the electrode directly or indirectly.

It is possible to use, for example, an electrode for detecting hydrogen peroxide as the aforementioned electrode for detection. More specifically, examples may include an enzyme electrode for detecting hydrogen peroxide and a separating membrane electrode for detecting hydrogen peroxide. In this case, the analysis of glycine becomes possible by detecting hydrogen peroxide produced when glycine is oxidized by a glycine oxidation activity. Configurations employed in known sensors can be utilized directly or by appropriately being modified as the configurations other than those above.

EXAMPLES

The present invention will be described in detail with reference to the following Examples, but the present invention is not limited thereto.

Example 1: Synthesis of GlyOX Using Cell-Free Synthesis System and Purification of GlyOX A histidine tag and a TEV protease recognition sequence were fused via a 2-step PCR to an N-terminal side of a wild-type GlyOX gene derived from *Bacillus subtilis* 168 strain, or an objective mutant gene, and used as a template to prepare linear DNA that has been introduced with the objective mutation. A protein was synthesized in a cell-free synthesis reaction system derived from *Escherichia coli* using this DNA as the template. A supernatant fraction obtained after centrifugation of a product synthesized by a dialysis method for 6 hours using 1 mL of a reaction scale was purified with histidine tag affinity for Ni Sepharose High Performance (GE Healthcare Japan) to yield an elution fraction. Subsequently, the possible presence of a protein identified as the objective enzyme was determined by SDS-PAGE and staining using SYPRO ORANGE protein gel stain (Life Technologies Japan Ltd.). The protein was quantified by the Bradford method, and subsequently evaluated. For the wild-type enzyme, the preparation of linear DNA, the cell-free synthesis, and the purification and analysis of the enzyme were performed in the same manner as above. The following buffers were used for the purification.

Binding buffer: 750 mM NaCl, 20 mM NaPi, pH 8.0
Washing buffer: 750 mM NaCl, 20 mM NaPi, pH 8.0
Recovery and measurement buffer: 300 mM NaCl, 50 mM NaPi, 34 mM EDTA, pH 7.0, 10% $D_2O$, 0.01% $NaN_3$ When a plurality of mutations are introduced into a GlyOX, each of the introduced mutations was marked off using a slash and described consecutively. For example, a mutant T42A/C245S denotes a mutant GlyOX having two mutations of T42A and C245S. WT denotes a wild-type enzyme.

Example 2: Measurement of Activity

Activity of the wild-type GlyOX and the mutant GlyOX synthesized in Example 1 was evaluated by the following procedure. First, the following reaction solutions A and B were prepared.

Reaction solution A: 4 mM phenol, 100 mM potassium phosphate, pH 8.0
Reaction solution B: 50 mM 4-aminoantipyrine, 500 U/mL peroxidase Subsequently, using a 96 well microplate, 49 µL of the reaction solution A, 1 µL of the reaction solution B, 10 µL of 2.5 mM Gly or 100 mM Gly, 20 µL of ultrapure water, and 20 µL of 0.5 mg/mL GlyOX were mixed to prepare a solution, and the change of absorbance at a wavelength of 500 nm of the solution at 25° C. after 3 minutes was measured using a microplate reader (SpectraMax M2e, Molecular Device Japan). The activity of each mutant GlyOX was shown as a ratio relative to the activity of the wild-type GlyOX in Tables 7 and 8. Each value was calculated from a mean value when the experiment was performed three times for the same sample. Table 7 and 8 show the results for the proteins synthesized using the wild-type gene and the objective mutant gene as the template, respectively when the linear DNA was prepared.

TABLE 7

Relative activity of each mutant GlyOX relative to wild-type

| | Relative activity relative to wild-type Gly concentration in reaction system | |
|---|---|---|
| | 0.25 mM | 10 mM |
| T42A | 2.59 | 1.05 |
| T42S | 1.03 | 1.35 |
| C245A | 0.29 | 0.87 |
| C245D | 0.04 | 0.07 |
| C245G | 0.12 | 0.38 |
| C245H | 0.36 | 0.93 |
| C245N | 0.19 | 0.58 |
| C245S | 0.41 | 0.84 |
| C245W | 0.06 | 0.26 |
| C245Y | 0.18 | 0.72 |
| L301A | 0.58 | 0.34 |
| L301I | 2.57 | 1.02 |
| L301N | 0.12 | 0.05 |

TABLE 7-continued

Relative activity of each mutant GlyOX relative to wild-type

| | Relative activity relative to wild-type Gly concentration in reaction system | |
|---|---|---|
| | 0.25 mM | 10 mM |
| L301S | 0.11 | 0.07 |
| L301V | 4.19 | 0.87 |

TABLE 8

Relative activity of each mutant GlyOX relative to wild-type

| | Relative activity relative to wild type Gly concentration in reaction system | |
|---|---|---|
| | 0.25 mM | 10 mM |
| T42C | 2.78 | 0.59 |
| T42G | 2.94 | 0.97 |
| L301C | 3.64 | 0.56 |
| L301P | 0.47 | 0.81 |
| L301T | 3.90 | 0.75 |
| T42A/C245S | 1.37 | 0.60 |
| T42A/L301C | 4.84 | 0.28 |
| T42A/L301V | 3.74 | 0.44 |
| T42S/C245S | 0.30 | 1.00 |
| T42S/L301C | 2.47 | 0.15 |
| T42S/L301V | 4.80 | 0.56 |
| C245S/L301C | 1.23 | 0.13 |
| C245S/L301V | 3.31 | 0.48 |
| T42A/C245S/L301V | 3.33 | 0.42 |
| T42S/C245S/L301C | 1.40 | 0.09 |
| T42S/C245S/L301V | 3.10 | 0.62 |

Example 3: Evaluation of Stability

Stability of the wild-type enzyme and the mutant enzyme synthesized in Example 1 was evaluated by the following procedure. 0.5 mg/mL of GlyOX was dispensed in a microtube and incubated at 4° C., 40° C., 50° C. and 60° C. for one hour. Subsequently, each enzyme solution was reacted under the same conditions as in Example 2 except that 100 mM Gly substrate solution was added. An activity was determined from the change of absorbance 10 minutes after starting the reaction. The stability was evaluated by determining the remaining activity as a ratio relative to the activity of an enzyme solution incubated at 4° C. The results are shown in Tables 9 and 10. Each value for GlyOX having mutated L301 in Table 9 was calculated from a mean value when the experiment was performed twice for the same sample. Each value for GlyOX other than those above was calculated from a mean value when the experiment was performed three times for the same sample. Table 9 and 10 show the results for the proteins synthesized using the wild-type gene and the objective mutant gene as the template, respectively when the linear DNA was prepared.

TABLE 9

Remaining activity of wild-type and each mutant GlyOX after heating for one hour.

| | Remaining activity Incubation temperature | | |
|---|---|---|---|
| | 40° C. | 50° C. | 60° C. |
| C245D | 1.07 | 0.50 | 0.00 |
| C245G | 1.03 | 0.63 | 0.01 |
| C245H | 0.97 | 0.71 | 0.01 |
| C245N | 0.99 | 0.66 | 0.01 |
| C245W | 1.05 | 0.94 | 0.12 |
| C245Y | 1.05 | 0.68 | 0.02 |
| L301A | 0.87 | 0.31 | 0.02 |
| L301N | 0.88 | 0.27 | 0.03 |
| L301S | 0.85 | 0.37 | 0.03 |
| WT | 0.95 | 0.52 | 0.01 |

TABLE 10

Remaining activity of wild-type and each mutant GlyOX after heating for one hour.

| | Remaining activity Incubation temperature | | |
|---|---|---|---|
| | 40° C. | 50° C. | 60° C. |
| T42A | 0.99 | 0.92 | 0.19 |
| T42S | 1.00 | 0.93 | 0.32 |
| T42C | 0.92 | 0.32 | 0.00 |
| T42G | 1.02 | 0.87 | 0.01 |
| C245A | 0.93 | 0.73 | 0.01 |
| C245S | 0.97 | 0.82 | 0.04 |
| L301C | 0.97 | 0.68 | 0.00 |
| L301I | 0.98 | 0.90 | 0.06 |
| L301V | 0.98 | 0.94 | 0.13 |
| L301P | 1.00 | 0.87 | 0.00 |
| L301T | 0.93 | 0.43 | 0.00 |
| T42A/C245S | 0.96 | 0.95 | 0.56 |
| T42A/L301C | 0.99 | 0.89 | 0.03 |
| T42A/L301V | 0.95 | 0.96 | 0.39 |
| T42S/C245S | 1.04 | 0.97 | 0.75 |
| T42S/L301C | 1.00 | 0.78 | 0.00 |
| T42S/L301V | 0.97 | 0.94 | 0.10 |
| C245S/L301C | 0.99 | 0.89 | 0.01 |
| C245S/L301V | 0.98 | 0.95 | 0.55 |
| T42A/C245S/L301V | 0.98 | 0.96 | 0.74 |
| T42S/C245S/L301C | 1.00 | 0.90 | 0.00 |
| T42S/C245S/L301V | 0.96 | 0.94 | 0.56 |
| WT | 0.97 | 0.69 | 0.01 |

Example 4: Expression System for GlyOX Using *Escherichia coli* and Purification of GlyOX A recombinant expression system for GlyOX was constructed using *Escherichia coli*. First, a plasmid for recombinant expression was constructed. An objective gene was amplified by a standard PCR method using a DNA primer 1 (TAATTCCATGGCTAAAAGGCATTATGAAGCAGTG-GTGATTG: SEQ ID NO:3) and a DNA primer 2 (TAATACTCGAGTATCTGAACCGCCTCCTTGCGATC: SEQ ID NO:4). Subsequently, the PCR product and pET-28a (Merck KGaA) were digested with restriction enzymes, NcoI (Takara Bio Inc.) and XhoI (Takara Bio Inc.). The digested PCR product and pET-28a were subjected to dephosphorylation with alkaline phosphatase (*E. coli* C75) (Takara Bio Inc.). Subsequently, deproteination and removal of unnecessary digestion fragments were carried out using QIAquick PCR Purification kit (Qiagen). Both the resulting products were ligated using Ligation High Ver. 2 (Toyobo Co., Ltd.). *Escherichia coli* DH5a strain was transformed with the ligation product using a standard method to obtain a transformant. A plasmid was extracted from the resulting transformant of DH5a, and insertion of the objective gene into the plasmid was identified using a standard analysis method of a DNA sequence. This plasmid having the inserted objective gene was referred to as pET-28a-GlyOX, and the transformant of BL21 (DE3) transformed with pET28a-GlyOX is referred to as pET28a-GlyOX-BL21 (DE3) hereinafter.

GlyOX was prepared as follows. First, the transformant pET28a-GlyOX-BL21 (DE3) from a glycerol stock thereof was inoculated on an LB plate containing 25 µg/mL of kanamycin, and statically cultured at 37° C. overnight. Subsequently 50 mL of an LB medium containing 25 µg/mL of kanamycin was placed in a 250 mL volume flask with a baffle, a single colony on the LB plate was inoculated thereto, and the colony in the medium was cultured at 37° C. overnight with rotary shaking. Then, 2 L of the LB medium containing 25 µg/mL of kanamycin was placed in a 5 L volume flask with a baffle, the above medium cultured overnight was entirely added to the flask, and IPTG at a final concentration of 0.5 mM was added when a value at OD660 reached 0.5 to 0.6. The cultivation was continued at 30° C. overnight with rotary shaking, then microbial cells were collected, washed with saline, suspended in buffer for disruption (20 mM Tris-HCl, 0.02 µM flavin adenine dinucleotide, pH 8.0), and treated using an ultrasonic disruption apparatus (201M, supplied from Kubota Corporation) at 180 W for 20 minutes. This solution of disrupted microbial cells was centrifuged at 12,000×g for 30 minutes, and a supernatant was collected. The supernatant was added to Ni Sepharose 6 Fast Flow (supplied from GE Healthcare Japan) equilibrated with washing buffer (50 mM HEPES, 500 mM NaCl, 20 mM imidazole, 0.02 µM flavin adenine dinucleotide, pH 7.5), which was then gently mixed with inversion at room temperature for 5 minutes. Subsequently, the solution was removed by free fall using an Econo-Pac column (supplied from Bio-Rad Laboratories Inc.). After washing with the washing buffer, the objective GlyOX protein was eluted with elution buffer (50 mM HEPES, 500 mM NaCl, 500 mM imidazole, 0.02 µM flavin adenine dinucleotide, pH 7.5). In the GlyOX solution, the solvent was replaced with stock buffer (50 mM potassium phosphate, 0.02 µM flavin adenine dinucleotide, pH 8.0) by ultrafiltration, and a concentration was adjusted to 0.5 mg/mL.

Example 5: Preparation of Mutant T42A/C245S/L301V Using *Escherichia coli*

A mutant T42A/C245S/L301V was prepared as follows. A mutation was introduced into a GlyOX gene using QuikChange Lightning Site-Directed Mutagenesis Kits (supplied from Agilent Technologies) and using pET28a-GlyOX as a template according to a protocol attached to the product. A plurality of mutations was introduced by adding another mutation using a plasmid already having the mutation as the template. The mutant T42A/C245S/L301V was obtained by performing recombinant expression, purification and solvent replacement according to the methods described in Example 4 using this plasmid already having the mutation.

Example 6: Preparation of Mutant Using *Escherichia coli*

An objective mutant was prepared as follows. A mutation was introduced into the GlyOX gene using QuikChange Lightning Site-Directed Mutagenesis Kits (supplied from Agilent Technologies) and using pET28a-GlyOX as the template according to the protocol attached to the product. A plurality of mutations was introduced by adding another mutation using a plasmid already having the mutation as the template. The objective mutant was obtained by performing recombinant expression, purification and solvent replacement according to the methods described below using this plasmid already having the mutation.

GlyOX was prepared as follows. First, the transformant pET28a-GlyOX-BL21 (DE3) from a glycerol stock thereof was inoculated to an LB plate containing 25 μg/mL of kanamycin, and statically cultured at 37° C. overnight.

Subsequently, 50 mL of LB medium containing 25 μg/mL of kanamycin was placed in a 250 mL volume flask with a baffle, a single colony on the LB plate was inoculated thereto, and the colony in the medium was cultured at 37° C. overnight with rotary shaking. Then, 1 L of the LB medium containing 25 μg/mL of kanamycin was placed in a 5 L volume flask with a baffle, 10 mL of the above medium cultured overnight was added to the flask, and IPTG at a final concentration of 0.5 mM was added when a value at OD660 reached 0.5 to 0.6. The cultivation was continued at 30° C. overnight with rotary shaking, then microbial cells were collected, washed with saline, suspended in buffer for disruption (20 mM Tris-HCl, 0.02 μM flavin adenine dinucleotide, pH 8.0), and treated using an ultrasonic disruption apparatus (201M, supplied from Kubota Corporation) at 180 W for 20 minutes. This solution of disrupted microbial cells was centrifuged at 12,000×g for 30 minutes, and a supernatant was collected. The supernatant was added to HisTRap FF Crude (supplied from GE Healthcare Japan) equilibrated with washing buffer (50 mM HEPES, 500 mM NaCl, 20 mM imidazole, 0.02 μM flavin adenine dinucleotide, pH 7.5). After washing with the washing buffer, the objective GlyOX protein was eluted with elution buffer (50 mM HEPES, 500 mM NaCl, 500 mM imidazole, 0.02 μM flavin adenine dinucleotide, pH 7.5). In the GlyOX solution, the solvent was replaced with stock buffer (50 mM potassium phosphate, 0.02 μM flavin adenine dinucleotide, pH 8.0) by ultrafiltration, and a concentration was adjusted to 0.5 mg/mL.

Example 7: Measurement of Activity

An activity was evaluated for the wild-type enzyme and mutant GlyOX synthesized in Example 6. Specifically, in the composition shown in Example 2, the enzyme solution was replaced with the GlyOX solution prepared in Example 6. The results are shown in Table 11.

TABLE 11

Relative activity of each mutant GlyOX relative to wild-type enzyme

| | Relative activity relative to wild type Gly concentration* | |
|---|---|---|
| | 0.25 mM | 10 mM |
| M49I | 0.29 | 0.29 |
| S190R | 0.84 | 0.81 |
| G304Y | 0.77 | 0.88 |
| S44K | 1.02 | 0.96 |
| T42A/C245S/L301V/M49I | 0.24 | 0.06 |
| T42A/C245S/L301V/S190R | 0.84 | 0.24 |
| T42A/C245S/L301V/G304Y | 0.92 | 0.80 |

TABLE 11-continued

Relative activity of each mutant GlyOX relative to wild-type enzyme

| | Relative activity relative to wild type Gly concentration* | |
|---|---|---|
| | 0.25 mM | 10 mM |
| T42A/C245S/L301V/S44K | 1.11 | 0.31 |
| T42A/C245S/L301V/G304Q | 1.49 | 0.84 |

*Gly concentration in reaction solution

Example 8: Evaluation of Stability

Stability was evaluated for the wild-type enzyme and mutant GlyOX synthesized in Example 6. Specifically, in the composition shown in Example 3, the enzyme solution was replaced with the GlyOX solution prepared in Example 6. The results are shown in Table 12.

TABLE 12

Remaining activity of wild-type and each mutant GlyOX after heating for one hour.

| | Remaining activity Incubation temperature | | |
|---|---|---|---|
| | 40° C. | 50° C. | 60° C. |
| M49I | 0.91 | 0.74 | 0.25 |
| S190R | 0.89 | 0.70 | 0.05 |
| G304Y | 0.90 | 0.65 | 0.02 |
| S44K | 0.91 | 0.70 | 0.04 |
| T42A/C245S/L301V/M49I | 0.96 | 0.92 | 0.36 |
| T42A/C245S/L301V/S190R | 0.88 | 0.79 | 0.18 |
| T42A/C245S/L301V/G304Y | 0.91 | 0.81 | 0.42 |
| T42A/C245S/L301V/S44K | 0.90 | 0.77 | 0.16 |
| T42A/C245S/L301V/G304Q | 0.89 | 0.79 | 0.37 |
| WT | 0.92 | 0.66 | 0.01 |

Example 9: Preparation of Mutant T42A/C245S/L301V/G304Q Using *Escherichia coli*

A mutant T42A/C245S/L301V/G304Q was prepared in the same way as in Example 5.

Example 10: Evaluation of Substrate Specificity

Figure 2:
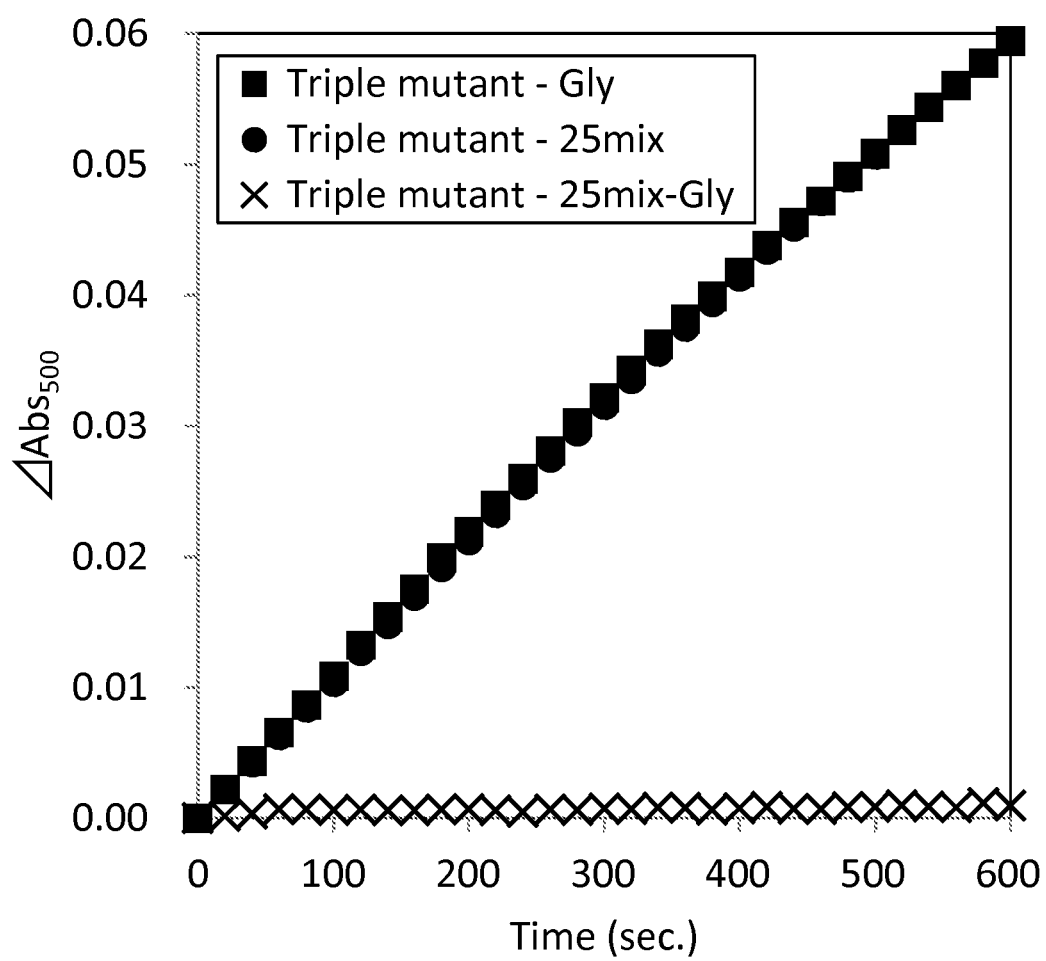
FIG. 2 shows substrate specificity of a mutant glycine oxidase for glycine (T42A/C245S/L301V).
Figure 3:
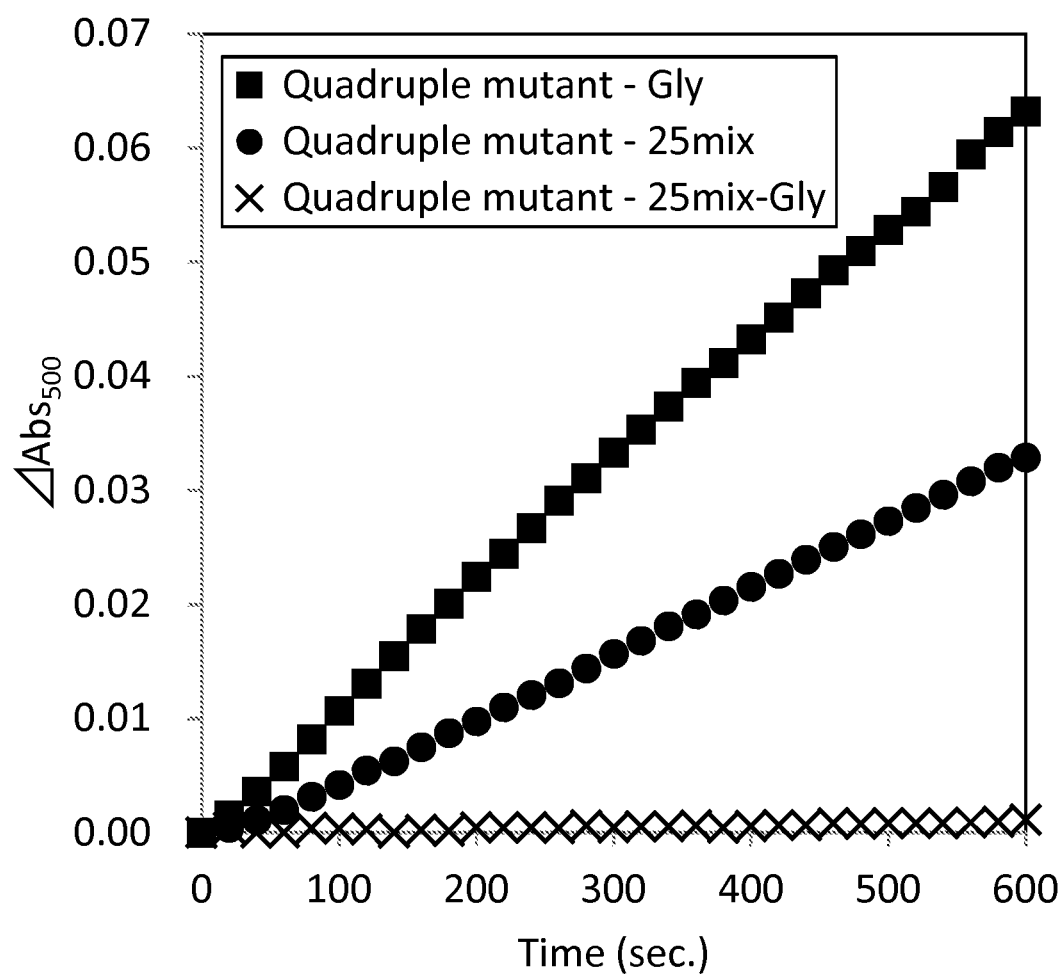
FIG. 3 shows substrate specificity of a mutant glycine oxidase for glycine (T42A/C245S/L301V/G304Q).

A substrate specificity was evaluated for the wild-type enzyme, the mutant T42A/C245S/L301V and the mutant T42A/C245S/L301V/G304Q. Specifically, in the composition shown in Example 2, the enzyme solution was replaced with the GlyOX solution prepared in Example 4, 5 or 9. As the substrate, (1) 1 mM Gly, (2) a mixed solution containing twenty standard amino acids, and cystine, taurine, citrulline, ornithine and α-aminobutyric acid each at 1 mM, or (3) a solution obtained by subtracting Gly from (2) the mixed solution of 25 amino acids was used in place of the Gly solution. Using these solutions, an enzymatic activity was measured for the evaluation. Try and cystine were dissolved in a 2 M HCl solution and the amino acids other than them were dissolved in a 0.1 M HCl solution to prepare a 100 mM solution. The respective amino acid solutions were mixed and then the resulting mixed solution was diluted with ultrapure water to 100 folds to prepare a mixed amino acid solution. On this occasion, the 2 M HCl solution and/or the 0.1 M HCl solution was mixed in place of the amino acid solutions not to be mixed in (1) and (3). The activity was obtained by detecting the change of an absorbance at a wavelength of 500 nm ($\Delta Abs_{500}$) at 37° C. using a microplate reader. The results for the wild-type, the mutant T42A/C245S/L301V and the mutant T42A/C245S/L301V/G304Q are shown in FIGS. 1, 2 and 3, respectively. Conditions for the substrate of (1), (2) and (3) above were represented as Gly, 25mix and 25mix-Gly, respectively. No catalytic activity for the amino acids other than Gly was observed in all of the wild-type, the mutant T42A/C245S/L301V and the mutant T42A/C245S/L301V/G304Q. When Gly was in the presence of the other amino acids, reaction inhibition due to the other amino acid(s) was observed in the wild-type and the mutant T42A/C245S/L301V/G304Q. The $\Delta Abs_{500}$ value of the wild-type 10 minutes after starting the reaction was 85% of when Gly alone was the substrate. The $\Delta Abs_{500}$ value of the mutant T42A/C245S/L301V/G304Q 10 minutes after starting the reaction was 52% of when Gly alone was the substrate. No reaction inhibition was observed in the mutant T42A/C245S/L301V, the nature of which was improved.

Figure 4:
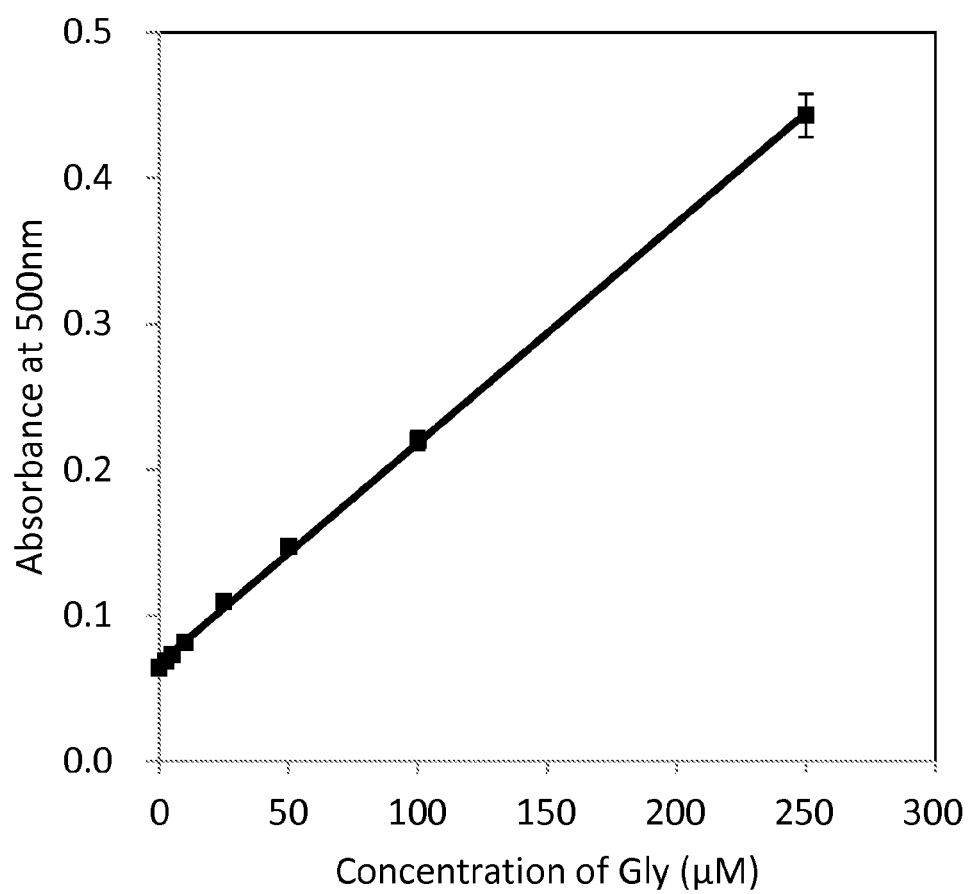
FIG. 4 shows the relationship between absorbance obtained by an endpoint method using the mutated glycine oxidase (T42A/C245S/L301V) and concentrations of Gly in a reaction solution.
Figure 5:
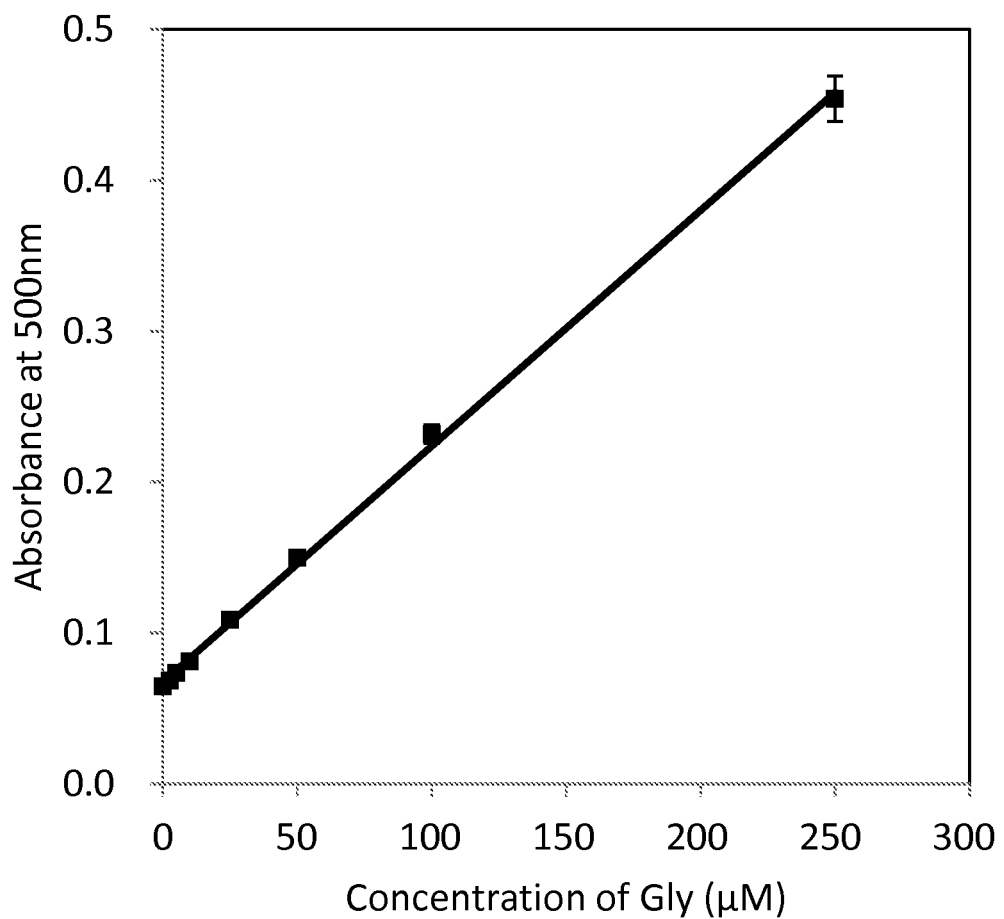
FIG. 5 shows the relationship between absorbance obtained by an endpoint method using the mutant glycine oxidase (T42A/C245S/L301V/G304Q) and concentrations of Gly in a reaction solution.

Example 11: Confirmation of Absorbance Change in Gly Concentration-Dependent Manner The relationship between Gly concentration and the absorbance obtained by an endpoint method in a reaction system was confirmed using the mutant T42A/C245S/L301V or the mutant T42A/C245S/L301V/G304Q. First, a reaction solution (4 mM phenol, 100 mM HEPES, pH 8.0) was prepared, and a solution was prepared by mixing 49 µL of the reaction solution, 1 µL of 50 mM 4-aminoantipyrine, 1 µL of 500 U/mL peroxidase, 10 µL of an aqueous solution of Gly at each concentration, 19 µL of ultrapure water and 20 µL of 4.0 mg/mL GlyOX. An absorbance of this solution at a wavelength of 500 nm after 10 minutes was measured using the microplate reader. This experiment was carried out three times, and a mean value was obtained. The GlyOX solution prepared in Example 5 or 9 was used as the enzyme solution. The aqueous solutions of Gly prepared at concentrations of 0 mM (i.e., ultrapure water), 0.025 mM, 0.05 mM, 0.1 mM, 0.25 mM, 0.5 mM, 1 mM and 2.5 mM were used. The relation between the Gly concentration and the absorbance in the reaction system exhibited a good positive correlation as shown in FIG. 4 or 5, indicating that Gly can be measured using the present enzyme. An error bar in FIG. 4 or 5 denotes the standard deviation.

Example 12: Quantitative Analysis of Gly in Plasma

Levels of Gly in human plasma were quantitatively analyzed using the mutant T42A/C245S/L301V or the mutant T42A/C245S/L301V/G304Q. The reaction and the measurement were carried out at 37° C. using cuvettes. A solution was prepared by mixing 441 µL of the reaction solution C in Example 11, 9 µL of 50 mM 4-aminoantipyrine, 9 µL of 500 U/mL peroxidase, 171 µL of ultrapure water, and 90 µL of the Gly solution at each concentration or human plasma as a specimen to be measured (total volume 720 µL). An absorbance at a wavelength of 500 nm or 800 nm was measured before or 10 minutes after 180 µL of 4.0 mg/mL GlyOX was added to this solution (Abs500 nm (before), Abs500 nm (after), Abs800 nm (before), Abs800 nm (after)). The GlyOX solution prepared in Example 5 or 9 was used as the enzyme solution. The Gly aqueous solutions prepared at concentrations of 0 M (i.e., ultrapure water), 0.25 mM and 0.5 mM were used.

Values of Abs500 nm–Abs800 nm were used as the absorbance values at each measurement point before and after the reaction. The change in the absorbance before and after adding the enzyme ($\Delta Abs$) was obtained as [Abs500 nm (after)–Abs800 nm (after)]–[Abs500 nm (before)–Abs800 nm (before)]×720/900. A standard curve was made from the relation between $\Delta Abs$ and the Gly concentration when the Gly solution was used as the specimen, and the Gly concentration in human plasma was obtained from $\Delta Abs$ when human plasma was used as the specimen. The standard curve was made using mean values obtained when the experiment at each Gly concentration was carried out three times. The values obtained by analyzing six times a human plasma sample in the same lot were compared to an analysis value (332 µM) obtained using an amino acid analyzer. This was used as a method 1 and the results are shown in Tables 13 and 14. Also for example, as described in a package insert of DIACOLOR Liquid BTR (supplied from Toyobo Co., Ltd.), a pharmaceutical for in-vitro diagnosis having an identification number No. 221AAAMX00010000, a method (method 2) of obtaining a concentration from a ratio of an absorbance value based on a component subjected to an analysis in a specimen to an absorbance value based on a component subjected to an analysis at known concentration is available. The results of the Gly concentrations obtained by this method 2 are shown together in Tables 13 and 14. Results that were good in correctness and elaboration were obtained using both the methods, showing that the Gly concentration in the human plasma can be quantitatively analyzed with good accuracy by using the Gly measurement system using the mutant GlyOX.

TABLE 13

Analysis results of Gly concentrations in human plasma using mutant GlyOX T42A/C245S/L301V, and gap ratios from analysis value by amino acid analyzer (332 µM).

|  |  | 1 | 2 | 3 | 4 | 5 | 6 | Mean | C.V. % |
|---|---|---|---|---|---|---|---|---|---|
| Gly | Method 1 | 340 | 340 | 336 | 339 | 342 | 345 | 341 | 0.9 |
| concentration | Method 2 | 342 | 342 | 338 | 341 | 344 | 347 | 342 | 0.9 |
| Gap ratio (%) | Method 1 | 2.5 | 2.4 | 1.3 | 2.2 | 3.2 | 4.0 | 2.6 | — |
|  | Method 2 | 3.0 | 2.9 | 1.8 | 2.7 | 3.6 | 4.5 | 3.1 | — |

Gly concentration (µM)

TABLE 14

Analysis results of Gly concentrations in human plasma using mutant GlyOX T42A/C245S/L301V/G304Q, and gap ratios from analysis value by amino acid analyzer (332 μM).

|  |  | 1 | 2 | 3 | 4 | 5 | 6 | Mean | C.V. % |
|---|---|---|---|---|---|---|---|---|---|
| Gly concentration | Method 1 | 353 | 353 | 356 | 354 | 352 | 353 | 354 | 0.3 |
|  | Method 2 | 355 | 354 | 357 | 355 | 353 | 354 | 355 | 0.3 |
| Gap ratio (%) | Method 1 | 6.5 | 6.3 | 7.1 | 6.6 | 6.1 | 6.3 | 6.5 | — |
|  | Method 2 | 6.8 | 6.7 | 7.5 | 7.0 | 6.4 | 6.7 | 6.8 | — |

Gly concentration (μM)

INDUSTRIAL APPLICABILITY

The modified enzyme of the present invention is useful for the rapid and highly sensitive measurement of glycine and/or the production of glycine oxylate. The modified enzyme of the present invention is also useful as the liquid reagent. The modified enzyme of the present invention is further useful for the measurement specific for glycine. The analysis method of the present invention is useful for a wide range of fields such as biological investigation, health nutrition, medical treatment, food manufacture, and the like.

The invention claimed is:

1. A glycine oxidase enzyme comprising the amino acid sequence of SEQ ID No: 2, and also comprising a mutation of at least one amino acid residue, wherein said mutation results in the improvement of one or more properties of said glycine oxidase which are associated with measurement of glycine as compared to said glycine oxidase that does not comprise said mutation, wherein the one or more properties are selected from the group consisting of:
   (a) an activity of the glycine oxidase for glycine;
   (b) a thermal stability of the glycine oxidase; and
   (c) a substrate specificity of the glycine oxidase for glycine,
   wherein the mutation is selected from the group consisting of:
   (A) a substitution of the first threonine in a TTS motif with alanine, cysteine, or glycine,
   (B) a substitution of serine in the TTS motif with lysine,
   (C) a substitution of cysteine in an HCY motif with alanine, aspartic acid, glycine, histidine, asparagine, tryptophan, tyrosine, or serine,
   (D) a substitution of leucine in an LRP motif with isoleucine, valine, cysteine, threonine, or proline,
   (E) a substitution of serine with arginine in a SG motif located in at positions 190 to 204 of SEQ ID NO: 2,
   (F) a substitution of glycine in a POT motif with tyrosine or glutamine, and
   (G) combinations thereof;
   wherein the glycine oxidase enzyme may have supplemental mutations as long as said supplemental mutations maintain said improved property.

2. The glycine oxidase enzyme according to claim 1, wherein the glycine oxidase is derived from a bacteria of the genus *Bacillus*.

3. The glycine oxidase enzyme according to claim 1, wherein the supplemental mutations are substitutions, deletions, insertions, and/or additions of one or several amino acid residues.

4. The glycine oxidase enzyme according to claim 1, wherein the starting glycine oxidase enzyme has an amino acid sequence having 90% or more sequence identity to the amino acid sequence of SEC) ID NO: 2.

5. The glycine oxidase enzyme according to claim 1, wherein the supplemental mutations are substitutions, deletions, insertions, and/or additions of 1 to 40 amino acid residues.

6. A kit for analyzing glycine comprising the glycine oxidase enzyme according to claim 1.

7. The kit for analyzing glycine according to claim 6, further comprising a component selected from the group consisting of a butter solution, a reagent for detecting hydrogen peroxide, a reagent for detecting ammonia, a reagent for detecting glyoxylic acid, and combinations thereof.

8. A detection system for analyzing glycine comprising:
(a) a device, and
(b) the glycine oxidase enzyme according to claim 1.

9. The detection system for analyzing glycine according to claim 8, further comprising a component selected from the group consisting of a buffer solution, a reagent for detecting hydrogen peroxide, a reagent for detecting ammonia, a reagent for detecting glyoxylic acid, and combinations thereof; and wherein the device is a microchannel chip.

10. An enzyme sensor for analyzing glycine, comprising:
(a) an electrode for detection, and
(b) the glycine oxidase enzyme according to claim 1, wherein said glycine oxidase enzyme is immobilized or retained on the electrode for detection.

11. A method of analyzing glycine comprising:
A) obtaining a test sample, and
B) measuring glycine in the test sample by contacting the glycine oxidase enzyme according to claim 1 with said sample.

12. The method according to claim 11, wherein said measuring comprises additionally using 4-aminoantipyrine, phenol, and peroxidase.

13. A method of producing glyoxylic acid comprising forming the glyoxylic acid by contacting glycine with the glycine oxidase enzyme according to claim 1.

* * * * *